US012367961B2

(12) United States Patent
Shamir et al.

(10) Patent No.: US 12,367,961 B2
(45) Date of Patent: Jul. 22, 2025

(54) METHODS, SYSTEMS, AND APPARATUSES FOR FAST APPROXIMATION OF ELECTRIC FIELD DISTRIBUTION

(71) Applicant: Novocure GmbH, Root (CH)

(72) Inventors: Reuven Ruby Shamir, Haifa (IL); Zeev Bomzon, Haifa (IL)

(73) Assignee: Novocure GmbH, Baar (CH)

( * ) Notice: Subject to any disclaimer, the term of this patent is extended or adjusted under 35 U.S.C. 154(b) by 947 days.

(21) Appl. No.: 17/139,475

(22) Filed: Dec. 31, 2020

(65) Prior Publication Data

US 2021/0196943 A1 Jul. 1, 2021

Related U.S. Application Data

(60) Provisional application No. 62/955,678, filed on Dec. 31, 2019.

(51) Int. Cl.
| | |
|---|---|
| *A61B 5/055* | (2006.01) |
| *A61B 5/0522* | (2021.01) |
| *A61N 1/02* | (2006.01) |
| *G06F 18/214* | (2023.01) |
| *G06F 18/241* | (2023.01) |

(Continued)

(52) U.S. Cl.
CPC ........... *G16H 20/40* (2018.01); *A61B 5/0522* (2013.01); *A61B 5/055* (2013.01); *A61N 1/025* (2013.01); *G06F 18/2148* (2023.01); *G06F 18/241* (2023.01); *G06N 20/00* (2019.01); *G06T 7/0012* (2013.01); *G16H 10/60* (2018.01); *G16H 20/30* (2018.01); *G16H 30/40* (2018.01); *G16H 50/20* (2018.01); *A61N 1/0476* (2013.01); *A61N 1/36002* (2017.08); *G01R 33/5608* (2013.01); *G06T 2207/30024* (2013.01)

(58) Field of Classification Search
CPC .. A61N 1/025; A61N 1/36002; A61N 1/0476; A61B 5/0522; A61B 5/055; G06T 7/0012; G06T 2207/30024; G16H 10/60; G16H 20/30; G16H 20/40; G16H 30/40; G16H 50/20; G06F 18/2148; G06F 18/241; G06N 20/00; G01R 33/5608
See application file for complete search history.

(56) References Cited

U.S. PATENT DOCUMENTS

| | | | |
|---|---|---|---|
| 7,146,210 | B2 | 12/2006 | Palti |
| 7,565,205 | B2 | 7/2009 | Palti |

(Continued)

FOREIGN PATENT DOCUMENTS

| | | |
|---|---|---|
| CN | 109558912 A | 4/2019 |
| EP | 330 797 A3 | 9/1989 |

(Continued)

OTHER PUBLICATIONS

1. Author: Essam A. Rashed, Jose Gomez-Tames, Akimasa Hirata Title: "Deep learning-based development of personalized human head model with non-uniform conductivity for brain stimulation" Published: Oct. 2019.*

(Continued)

*Primary Examiner* — Rinna Yi
(74) *Attorney, Agent, or Firm* — McCarter & English, LLP; Michael A. Sartori

(57) ABSTRACT

Methods, systems, and apparatuses are described for fast approximation of electric field distribution.

20 Claims, 19 Drawing Sheets

(51) Int. Cl.

| | |
|---|---|
| *G06N 20/00* | (2019.01) |
| *G06T 7/00* | (2017.01) |
| *G16H 10/60* | (2018.01) |
| *G16H 20/30* | (2018.01) |
| *G16H 20/40* | (2018.01) |
| *G16H 30/40* | (2018.01) |
| *G16H 50/20* | (2018.01) |
| *A61N 1/04* | (2006.01) |
| *A61N 1/36* | (2006.01) |
| *G01R 33/56* | (2006.01) |

(56) References Cited

U.S. PATENT DOCUMENTS

| | | | |
|---|---|---|---|
| 10,188,851 B2 | 1/2019 | Wenger et al. | |
| 11,013,909 B2 | 5/2021 | Wenger et al. | |
| 11,154,707 B2 | 10/2021 | Bomzon et al. | |
| D934,892 S | 11/2021 | Hershkovich et al. | |
| 2012/0245653 A1* | 9/2012 | Bikson .................. | G16H 50/50 607/45 |
| 2018/0160933 A1 | 6/2018 | Urman et al. | |
| 2019/0117956 A1 | 4/2019 | Wenger et al. | |
| 2019/0117963 A1 | 4/2019 | Travers et al. | |
| 2019/0308016 A1 | 10/2019 | Wenger et al. | |
| 2020/0114141 A1 | 4/2020 | Bomzon et al. | |
| 2020/0129761 A1 | 4/2020 | Bomzon et al. | |
| 2020/0146586 A1 | 5/2020 | Naveh et al. | |
| 2020/0219261 A1 | 7/2020 | Shamir et al. | |
| 2020/0353245 A1 | 11/2020 | Travers et al. | |
| 2020/0372705 A1 | 11/2020 | Hershkovich et al. | |
| 2021/0060334 A1 | 3/2021 | Avraham et al. | |
| 2021/0162228 A1 | 6/2021 | Urman et al. | |
| 2021/0187277 A1 | 6/2021 | Wasserman et al. | |
| 2021/0196207 A1 | 7/2021 | Shamir et al. | |
| 2021/0196943 A1 | 7/2021 | Shamir et al. | |
| 2021/0201572 A1 | 7/2021 | Bomzon | |
| 2021/0299439 A1 | 9/2021 | Shamir et al. | |

FOREIGN PATENT DOCUMENTS

| | | |
|---|---|---|
| GB | 1 419 660 | 12/1975 |
| GB | 2 026 322 A | 2/1980 |
| GB | 2 043 453 A | 10/1980 |
| WO | 01/60994 A1 | 8/2001 |
| WO | 2010/120823 A2 | 10/2010 |
| WO | 2011/047387 A2 | 4/2011 |
| WO | 2017/072706 A1 | 5/2017 |
| WO | 2018/057529 A1 | 3/2018 |
| WO | WO-2018/109691 A2 | 6/2018 |
| WO | WO-2019/212804 A1 | 11/2019 |
| WO | 2020/168035 A1 | 8/2020 |
| WO | 2020/225599 A1 | 11/2020 |

OTHER PUBLICATIONS

Author: Yuefeng Wang, Manjari Pandey, Matthew T. Ballo, Title: "Integration of Tumor-Treating Fields into the Multidisciplinary Management of Patients with Solid Malignancies" Published: Aug. 23, 2019.*

Author: Pedro C. Miranda, María A. Callejón-Leblic, Ricardo Salvador, Giulio Ruffini, Title: "Realistic modeling of transcranial current stimulation- The electric field in the brain", Published: Sep. 2018.*

Author: Boateng Asamoah, Ahmad Khatoun, Myles Mc Laughlin, Title: "tACS motor system effects can be caused by transcutaneous stimulation of peripheral nerves", Published: Jan. 17, 2019.*

Author: John Harvey Kindred, Steven A Kautz, Elizabeth C. Wonsetler, Mark Goodman Bowden, Title: "Single Sessions of High-Definition Transcranial Direct Current Stimulation Do Not Alter Lower Extremity Biomechanical or Corticomotor Response Variables Poststroke", Published: Apr. 2019.*

"Real-time estimation of electric fields induced by transcranial magnetic stimulation with deep neural networks" by Yokota et al. published on Jun. 17, 2019.*

Ballo, et al., "Correlation of Tumor Treating Fields Dosimetry to Survival Outcomes in Newly Diagnosed 1 Glioblastoma: A Large-Scale Numerical Simulation-Based Analysis of Data from the Phase 3 EF-14 Randomized Trial," International Journal of Radiation Oncology, Biology, Physics, 2019; 104(5), pp. 1106-1113.

Huang et al., "Realistic volumetric-approach to simulate transcranial electric stimulation—ROAST—a fully automated open-source pipeline," Journal of Neural Engineering, vol. 16, No. 5 pp. 56006, 2019. [Cited in Search Report in counterpart Inter. Appl. No. PCT/IB2020/001117, dated May 14, 2021.].

Shamir, et al., "A Method for Tumor Treating Fields Fast Estimation," Arxiv.org, Cornell University, Oct. 6, 2020, p. 5-6, section 2.3; Figure 3. [Cited in Search Report in counterpart Inter. Appl. No. PCT/IB2020/001117, dated May 14, 2021.].

* cited by examiner

FIG. 7A
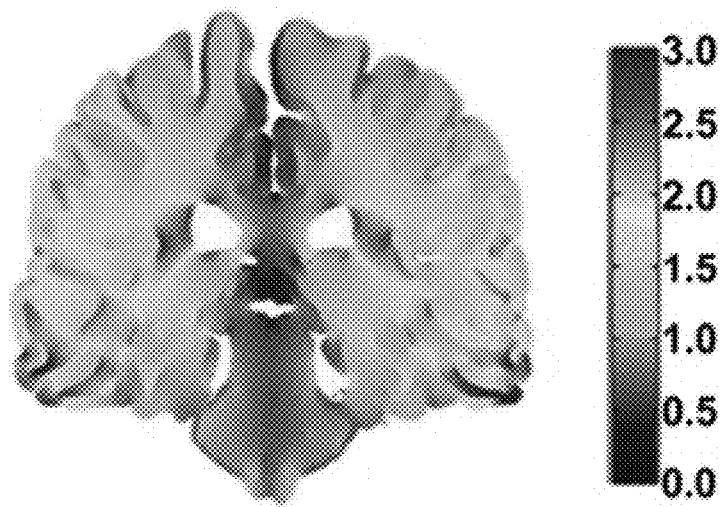
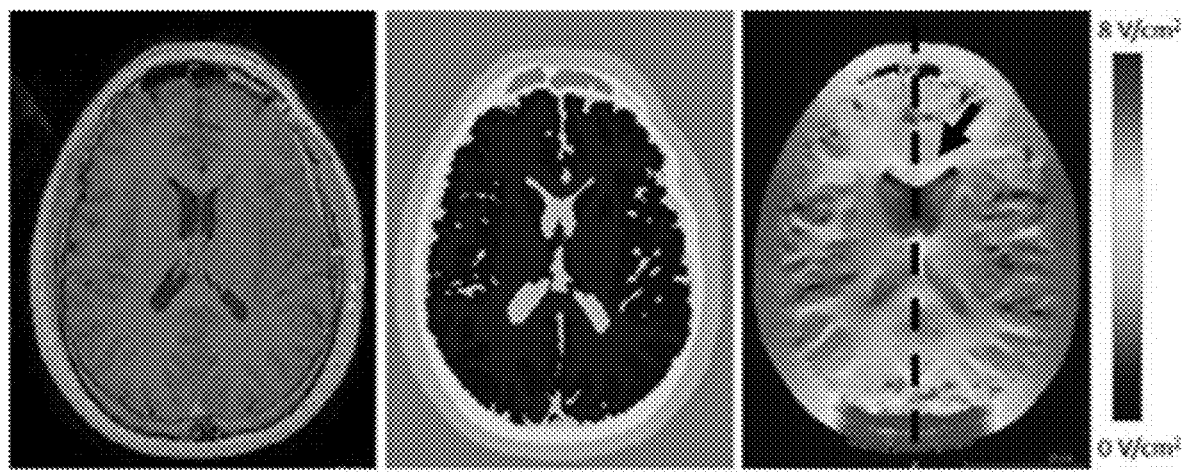
FIG. 7B          FIG. 7C          FIG. 7D

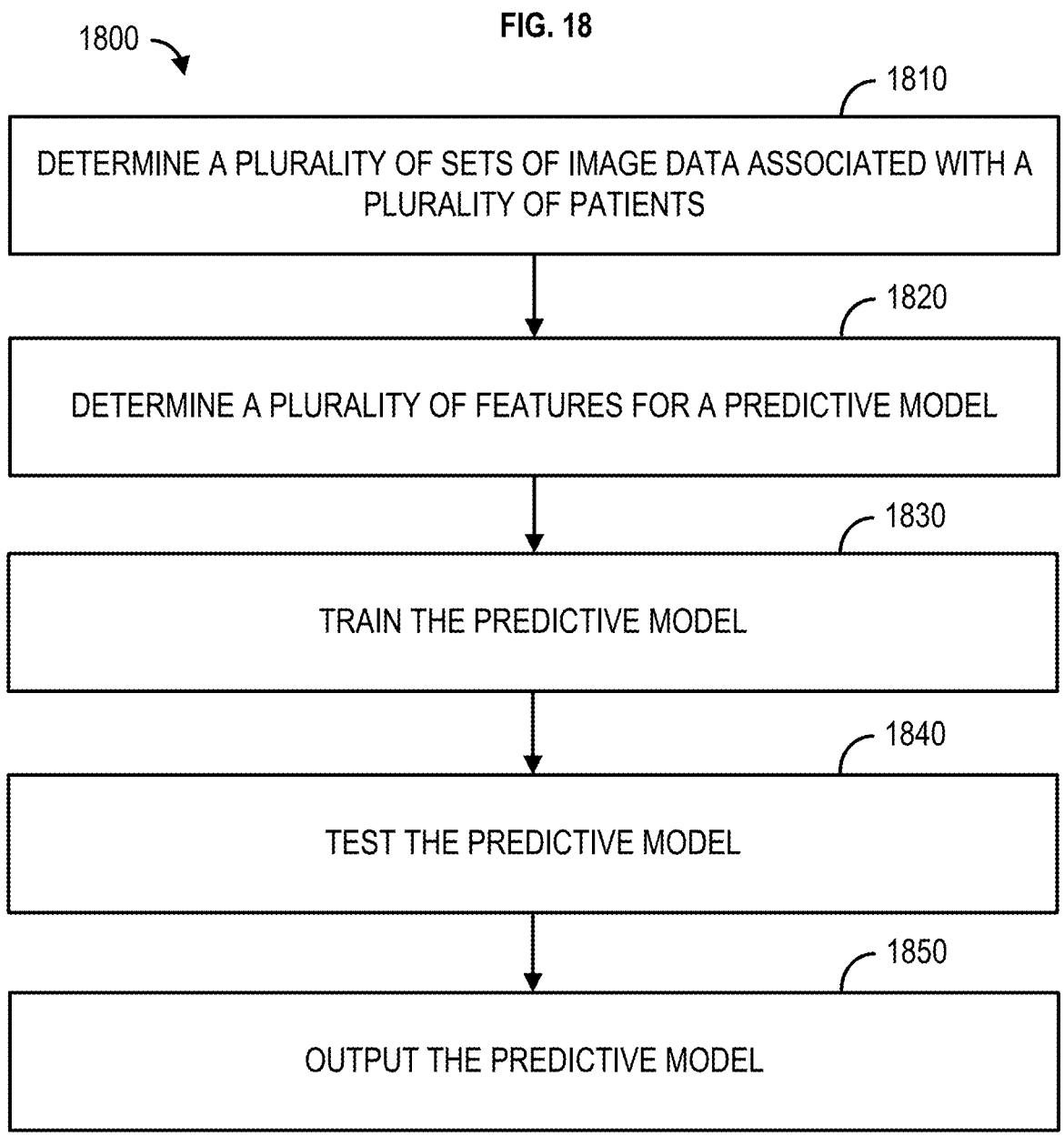

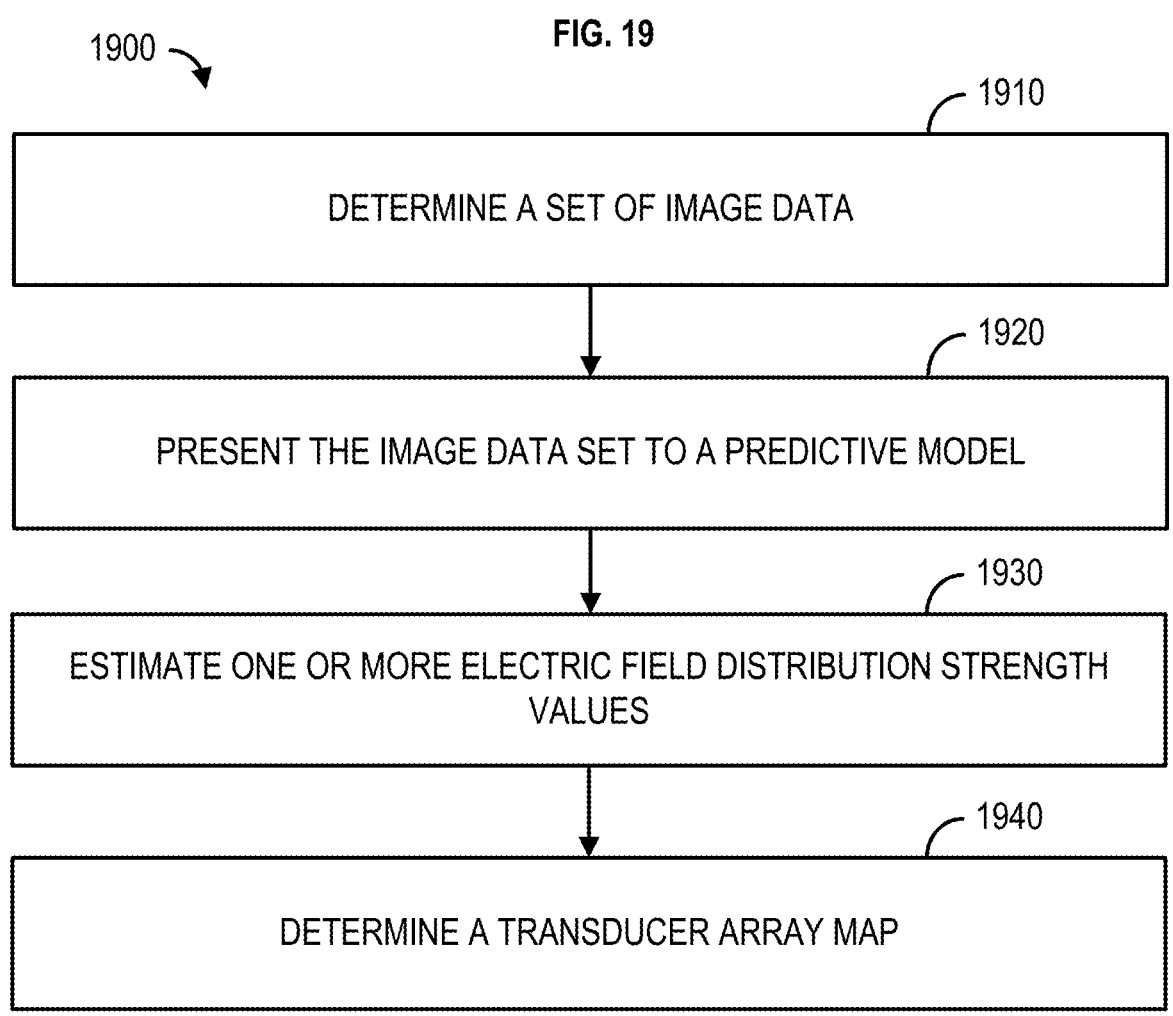

METHODS, SYSTEMS, AND APPARATUSES FOR FAST APPROXIMATION OF ELECTRIC FIELD DISTRIBUTION

CROSS-REFERENCE TO RELATED PATENT APPLICATION

This application claims priority to U.S. Provisional Application No. 62/955,678 filed Dec. 31, 2019, which is herein incorporated by reference in its entirety.

BACKGROUND

Tumor Treating Fields, or TTFields, are low intensity (e.g., 1-3 V/cm) alternating electric fields within the intermediate frequency range (100-300 kHz). TTFields therapy is a U.S. Food and Drug Administration (FDA) approved treatment for Glioblastoma Multiforme (GBM) and Malignant Pleural Mesothelioma (MPM). This non-invasive treatment targets solid tumors and is described in U.S. Pat. No. 7,565,205, which is incorporated herein by reference in its entirety. Clinical trials have shown that adding TTFields to a standard of care significantly extends Glioblastoma patient overall survival. Similar improvements have been observed in MPM patients. TTFields are delivered non-invasively using pairs of transducer arrays that are placed on the skin near the tumor. The arrays are connected to a field generator that when activated generates an alternating electric field in the range of 100-300 KHz that propagates into cancerous tissue. TTFields disrupt cell division through physical interactions with key molecules during mitosis. TTFields therapy is an approved mono-treatment for recurrent glioblastoma and approved combination therapy with chemotherapy for newly diagnosed patients. These electric fields are induced non-invasively by transducer arrays (i.e., arrays of electrodes) placed directly on the patient's scalp. TTFields also appear to be beneficial for treating tumors in other parts of the body. The distribution of the electric field produced by transducer arrays maximizes the benefits of TTFields therapy, but the optimal positioning of transducer arrays is not easily determined. Current methods for estimating TTFields intensity distributions rely on finite element methods that are time-consuming and may require hours to compute the field generated by a single pair of a transducer array. For example, estimation of the electric field distribution involves complex and time-consuming calculations that require, at minimum, 3-4 hours on a dedicated high-performance computer Hence, during any practical optimization scheme for TTFields treatment planning, only a limited number of transducer array locations can be evaluated and the optimization result may be suboptimal.

SUMMARY

Described are methods comprising determining a plurality of sets of image data associated with a plurality of patients, wherein each patient is associated with a set of image data derived from imaging a portion of the patient, wherein each set of image data comprises a plurality of voxels, wherein each voxel of the plurality of voxels is labeled with a tissue type, and wherein each voxel of the plurality of voxels is labeled with an electric field strength distribution value (V cm-1) derived from a simulated application of an alternating electric field from of a pair of transducer arrays to the portion of the patient, determining, based on a first portion of the plurality of sets of image data, a plurality of features for a predictive model, training, based on the plurality of features and the first portion of the plurality of sets of image data, the predictive model, wherein the predictive model is configured to estimate electric field strength distribution values, testing, based on a second portion of the plurality of sets of image data, the predictive model, and outputting, based on the testing, the predictive model.

Also described are methods comprising determining, for a patient, a set of image data, wherein the set of image data comprises a plurality of voxels, presenting, to a predictive model, the image data set, wherein the predictive model is configured to estimate electric field strength distribution values based on one or more simulated alternating electric fields from a pair of transducer arrays at a plurality of positions, estimating, by the predictive model, for each voxel of the plurality of voxels, one or more electric field distribution strength values for the pair of transducer arrays at each of a plurality of positions, and determining, based on the estimated one or more electric field distribution strength values for the pair of transducer arrays at each of the plurality of positions, a region of interest, and an anatomical restriction associated with the patient, a transducer array map comprising one or more positions of the plurality of positions.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

To easily identify the discussion of any particular element or act, the most significant digit or digits in a reference number refer to the figure number in which that element is first introduced.

FIG. 7A shows electric field magnitude and distribution (in V/cm) shown in coronal view from a finite element method simulation model.

FIGS. 7B-D show example simulation results.

FIG. 18 shows an example method.

FIG. 19 shows an example method.

DETAILED DESCRIPTION

Figure 1:
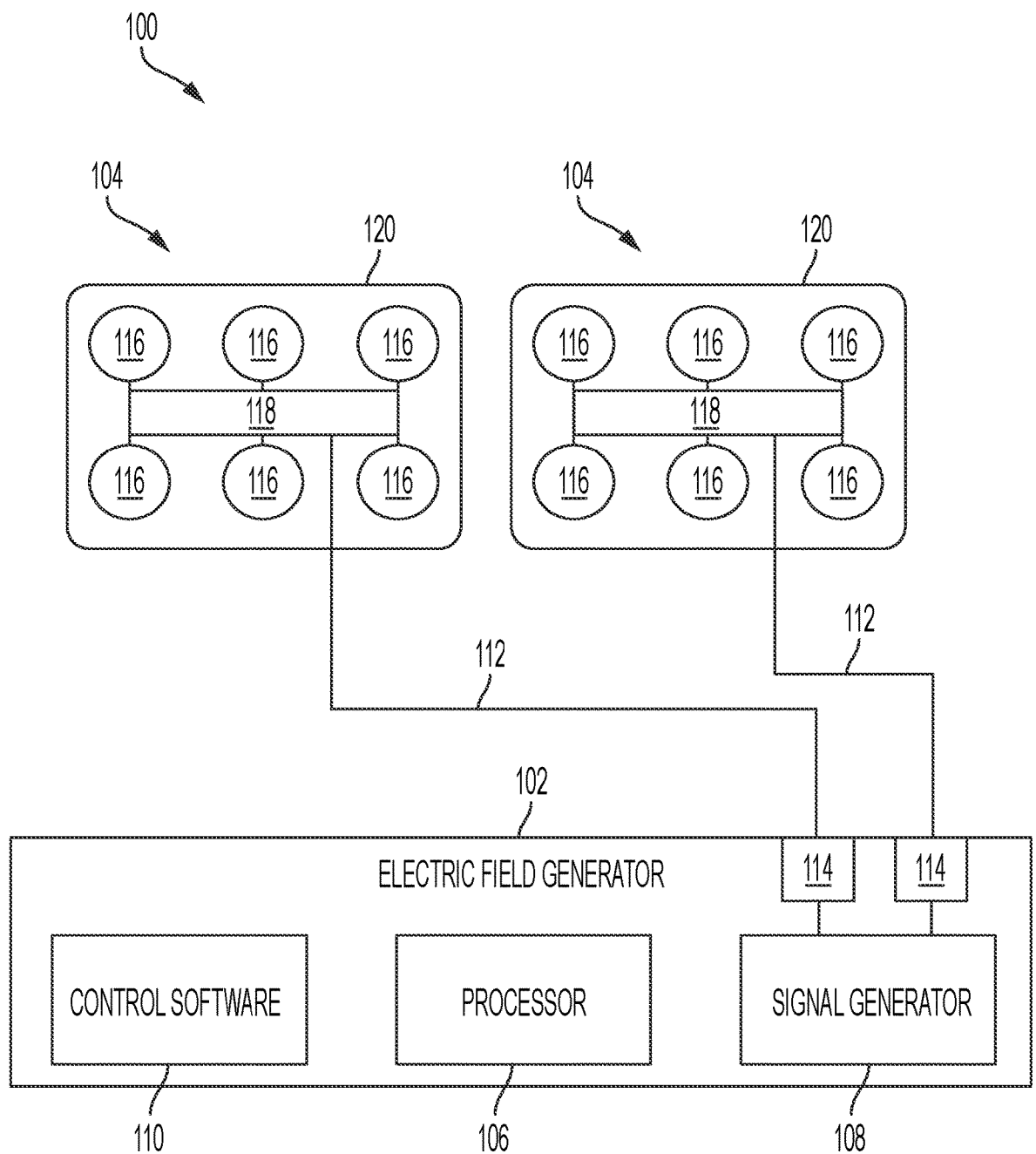
FIG. 1 shows an example apparatus for electrotherapeutic treatment.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses, and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

TTFields, also referred to herein as alternating electric fields, are established as an anti-mitotic cancer treatment modality because they interfere with a proper microtubule assembly during metaphase and eventually destroy the cells during telophase and cytokinesis. The efficacy increases with increasing field strength and the optimal frequency are cancer cell line dependent with 200 kHz being the frequency for which inhibition of glioma cell growth caused by TTFields is highest. For cancer treatment, non-invasive devices were developed with capacitively coupled transducers that are placed directly at the skin region close to the tumor, for example, for patients with Glioblastoma Multiforme (GBM), the most common primary, malignant brain tumor in humans.

Clinical trials have shown that adding TTFields to a standard of care significantly extends Glioblastoma patient overall survival. Similar improvements were observed in Malignant Pleural Mesothelioma (MPM) patients The post-hoc analysis of clinical data showed that delivery of higher field intensities to the tumor is associated with prolonged patient survival. Therefore, placing the transducer arrays such that the TTFields intensity is maximized in the cancerous tissue, has the potential of further extending patients' life.

Because the effect of TTFields is directional with cells dividing parallel to the field affected more than cells dividing in other directions, and because cells divide in all directions, TTFields are typically delivered through two pairs of transducer arrays that generate perpendicular fields within the treated tumor. More specifically, one pair of transducer arrays may be located to the left and right (LR) of the tumor, and the other pair of transducer arrays may be located anterior and posterior (AP) to the tumor. Cycling the field between these two directions (i.e., LR and AP) ensures that a maximal range of cell orientations is targeted. Other positions of transducer arrays are contemplated beyond perpendicular fields. In an embodiment, asymmetric positioning of three transducer arrays is contemplated wherein one pair of the three transducer arrays may deliver alternating electric fields and then another pair of the three transducer arrays may deliver the alternating electric fields, and the remaining pair of the three transducer arrays may deliver the alternating electric fields.

In-vivo and in-vitro studies show that the efficacy of TTFields therapy increases as the intensity of the electric field increases. Therefore, optimizing array placement on the patient's scalp to increase the intensity in the diseased region of the brain is standard practice for the Optune system. Array placement optimization may be performed by "rule of thumb" (e.g., placing the arrays on the scalp as close to the tumor as possible), measurements describing the geometry of the patient's head, tumor dimensions, and/or tumor location. Measurements used as input may be derived from imaging data. Imaging data is intended to include any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). Optimization can rely on an understanding of how the electric field distributes within the head as a function of the positions of the array and, in some aspects, take account for variations in the electrical property distributions within the heads of different patients. Described herein is a novel method that incorporates random forest regression (and/or other machine learning) for fast estimation of TTFields. As described herein, key parameters that affect TTFields intensity may be identified, and methods are described for extraction of these parameters. The use of random forest regression for fast estimation of the TTFields has been validated on GBM patients (at least 10 patients).

FIG. 1 shows an example apparatus 100 for electrotherapeutic treatment. Generally, the apparatus 100 may be a portable, battery or power supply operated device which produces alternating electric fields within the body through non-invasive surface transducer arrays. The apparatus 100 may comprise an electric field generator 102 and one or more transducer arrays 104. The apparatus 100 may be configured to generate tumor treatment fields (TTFields) (e.g., at 150 kHz) via the electric field generator 102 and deliver the TTFields to an area of the body through the one or more transducer arrays 104. The electric field generator 102 may be a battery and/or power supply operated device. In an embodiment, the one or more transducer arrays 104 are uniformly shaped. In an embodiment, the one or more transducer arrays 104 are not uniformly shaped.

The electric field generator 102 may comprise a processor 106 in communication with a signal generator 108. The electric field generator 102 may comprise control software 110 configured for controlling the performance of the processor 106 and the signal generator 108.

The signal generator 108 may generate one or more electric signals in the shape of waveforms or trains of pulses. The signal generator 108 may be configured to generate an alternating voltage waveform at frequencies in the range from about 50 kHz to about 500 kHz (preferably from about 100 KHz to about 300 KHz) (e.g., the TTFields). The voltages are such that the electric field intensity in tissue to be treated is in the range of about 0.1 V/cm to about 10 V/cm.

One or more outputs 114 of the electric field generator 102 may be coupled to one or more conductive leads 112 that are attached at one end thereof to the signal generator 108. The opposite ends of the conductive leads 112 are connected to the one or more transducer arrays 104 that are activated by the electric signals (e.g., waveforms). The conductive leads 112 may comprise standard isolated conductors with a flexible metal shield and may be grounded to prevent the spread of the electric field generated by the conductive leads 112. The one or more outputs 114 may be operated sequentially. Output parameters of the signal generator 108 may comprise, for example, an intensity of the field, a frequency of the waves (e.g., treatment frequency), and a maximum allowable temperature of the one or more transducer arrays 104. The output parameters may be set and/or determined by the control software 110 in conjunction with the processor 106. After determining a desired (e.g., optimal) treatment frequency, the control software 110 may cause the processor 106 to send a control signal to the signal generator 108 that causes the signal generator 108 to output the desired treatment frequency to the one or more transducer arrays 104.

The one or more transducer arrays 104 may be configured in a variety of shapes and positions to generate an electric field of the desired configuration, direction, and intensity at a target volume to focus treatment. The one or more transducer arrays 104 may be configured to deliver two perpendicular field directions through a volume of interest.

The one or more transducer arrays 104 arrays may comprise one or more electrodes 116. The one or more electrodes 116 may be made from any material with a high dielectric constant. The one or more electrodes 116 may comprise, for example, one or more insulated ceramic discs. The electrodes 116 may be biocompatible and coupled to a flexible circuit board 118. The electrodes 116 may be configured to not come into direct contact with the skin as the electrodes 116 are separated from the skin by a layer of conductive hydrogel (not shown) (similar to that found on electrocardiogram pads).

The electrodes 116, the hydrogel, and the flexible circuit board 118 may be attached to a hypoallergenic medical adhesive bandage 120 to keep the one or more transducer arrays 104 in place on the body and in continuous direct contact with the skin. Each transducer array 104 may comprise one or more thermistors (not shown), for example, 8 thermistors, (accuracy ±1° C.) to measure skin temperature beneath the transducer arrays 104. The thermistors may be configured to measure skin temperature periodically, for example, every second. The thermistors may be read by the control software 110 while the TTFields are not being delivered to avoid any interference with the temperature measurements.

If the temperature measured is below a pre-set maximum temperature (Tmax), for example, 38.5-40.0° C.±0.3° C., between two subsequent measures, the control software 110 can increase current until the current reaches maximal treatment current (for example, 4 Amps peak-to-peak). If the temperature reaches Tmax+0.3° C. and continues to rise, the control software 110 can lower the current. If the temperature rises to 41° C., the control software 110 can shut off the TTFields therapy and an overheating alarm can be triggered.

Figure 2:
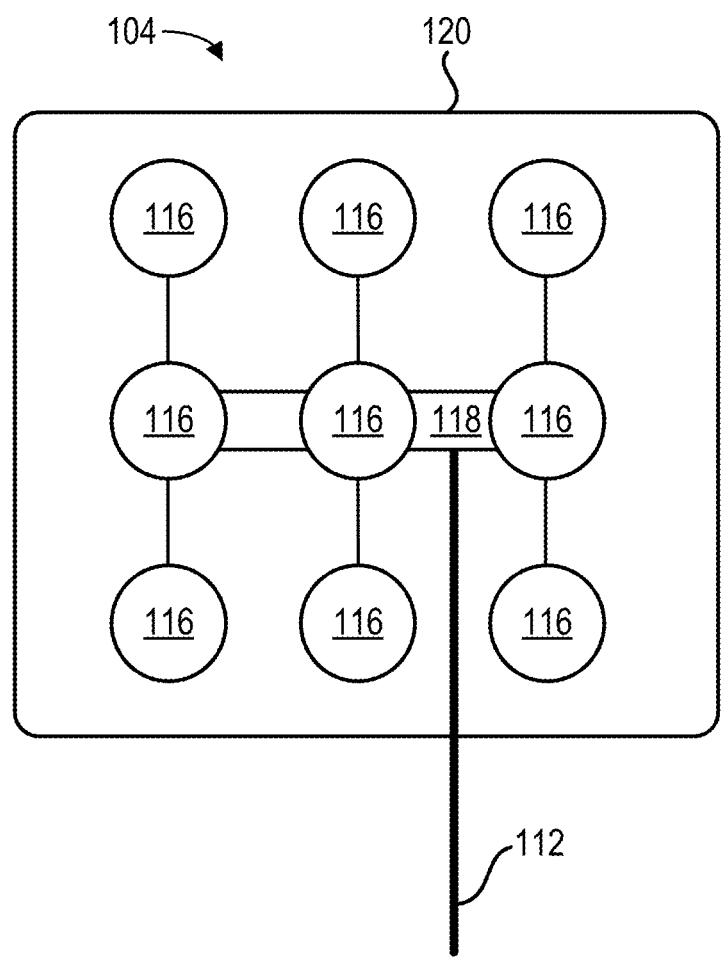
FIG. 2 shows an example transducer array.

The one or more transducer arrays 104 may vary in size and may comprise varying numbers of electrodes 116, based on patient body sizes and/or different therapeutic treatments. For example, in the context of the chest of a patient, small transducer arrays may comprise 13 electrodes each, and large transducer arrays may comprise 20 electrodes each, with the electrodes serially interconnected in each array. For example, as shown in FIG. 2, in the context of the head of a patient, each transducer array may comprise 9 electrodes each, with the electrodes serially interconnected in each array.

Alternative constructions for the one or more transducer arrays 104 are contemplated and may also be used, including, for example, transducer arrays that use ceramic elements that are not disc-shaped, and transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array would be implemented using a region of a conductive material that is configured for placement against a subject/patient's body, with no insulating dielectric layer disposed between the conductive elements and the body. Other alternative constructions for implementing the transducer arrays may also be used. Any transducer array (or similar device/component) configuration, arrangement, type, and/or the like may be used for the methods and systems described herein as long as the transducer array (or similar device/component) configuration, arrangement, type, and/or the like is (a) capable of delivering TTFields to the subject/patient's body and (b) and may be positioned arranged, and/or placed on a portion of a patient/subject's body as described herein.

A status of the apparatus 100 and monitored parameters may be stored in/by a memory (not shown) and can be transferred to a computing device over a wired or wireless connection. The apparatus 100 may comprise a display (not shown) for displaying visual indicators, such as, power on, treatment on, alarms, and low battery.

Figure 3A:
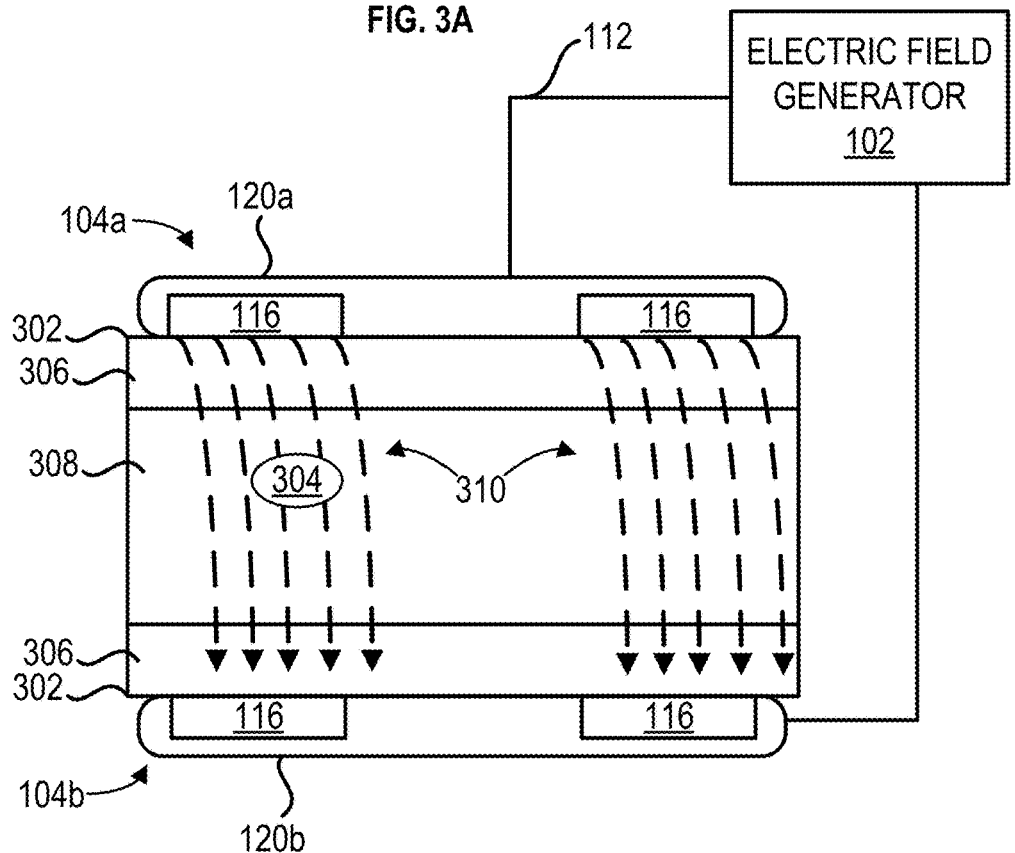
FIG. 3A and FIG. 3B show an example application of the apparatus for electrotherapeutic treatment.
Figure 3B:
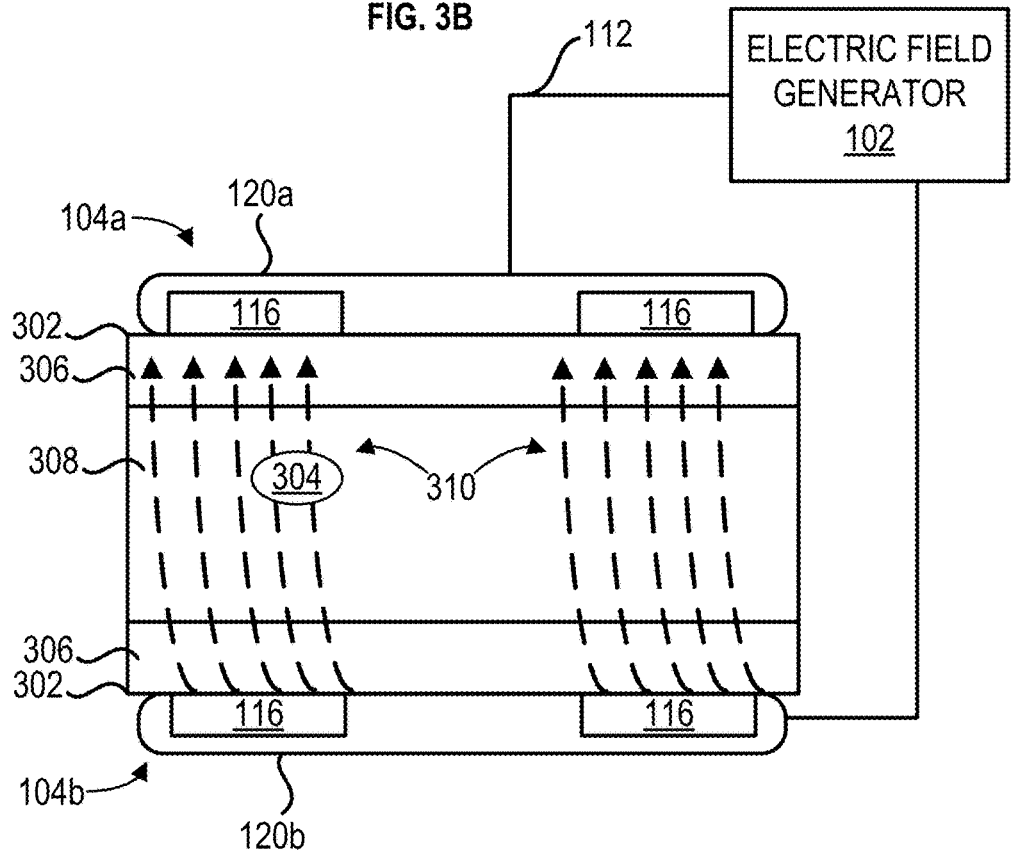

FIG. 3A and FIG. 3B illustrate an example application of the apparatus 100. A transducer array 104a and a transducer array 104b are shown, each incorporated into a hypoallergenic medical adhesive bandage 120a and 120b, respectively. The hypoallergenic medical adhesive bandages 120a and 120b are applied to skin surface 302. A tumor 304 is located below the skin surface 302 and bone tissue 306 and is located within brain tissue 308. The electric field generator 102 causes the transducer array 104a and the transducer array 104b to generate alternating electric fields 310 within the brain tissue 308 that disrupt rapid cell division exhibited by cancer cells of the tumor 304. The alternating electric fields 310 have been shown in non-clinical experiments to arrest the proliferation of tumor cells and/or to destroy them. Use of the alternating electric fields 310 takes advantage of the special characteristics, geometrical shape, and rate of dividing cancer cells, which make them susceptible to the effects of the alternating electric fields 310. The alternating electric fields 310 alter their polarity at an intermediate frequency (on the order of 100-300 kHz). The frequency used for a particular treatment may be specific to the cell type being treated (e.g., 150 kHz for MPM). The alternating electric fields 310 have been shown to disrupt mitotic spindle microtubule assembly and to lead to dielectrophoretic dislocation of intracellular macromolecules and organelles during cytokinesis. These processes lead to the physical disruption of the cell membrane and programmed cell death (apoptosis).

Because the effect of the alternating electric fields 310 is directional with cells dividing parallel to the field affected more than cells dividing in other directions, and because cells divide in all directions, alternating electric fields 310 may be delivered through two pairs of transducer arrays 104 that generate perpendicular fields within the treated tumor. More specifically, one pair of transducer arrays 104 may be located to the left and right (LR) of the tumor, and the other pair of transducer arrays 104 may be located anterior and posterior (AP) to the tumor. Cycling the alternating electric fields 310 between these two directions (e.g., LR and AP) ensures that a maximal range of cell orientations is targeted. In an embodiment, the alternating electric fields 310 may be delivered according to a symmetric setup of transducer arrays 104 (e.g., four total transducer arrays 104, two matched pairs). In another embodiment, the alternating electric fields 310 may be delivered according to an asymmetric setup of transducer arrays 104 (e.g., three total transducer arrays 104). An asymmetric setup of transducer arrays 104 may engage two of the three transducer arrays 104 to deliver the alternating electric fields 310 and then switch to another two of the three transducer arrays 104 to deliver the alternating electric fields 310, and the like.

In-vivo and in-vitro studies show that the efficacy of TTFields therapy increases as the intensity of the electric field increases. The methods, systems, and apparatuses described are configured for optimizing array placement on the patient's scalp to increase the intensity in the diseased region of the brain.

Figure 4A:
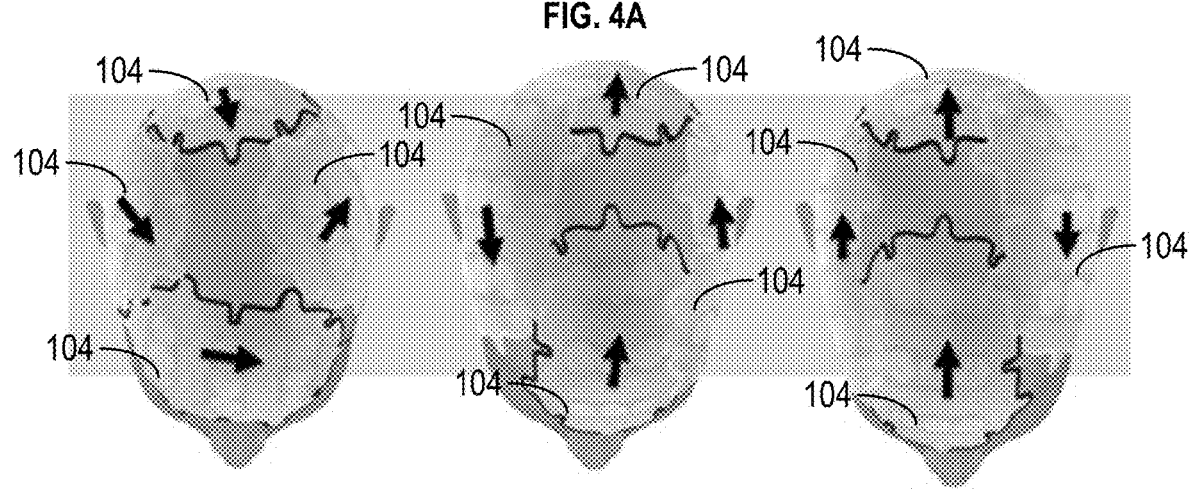
FIG. 4A shows transducer arrays placed on a patient's head.
Figure 4B:
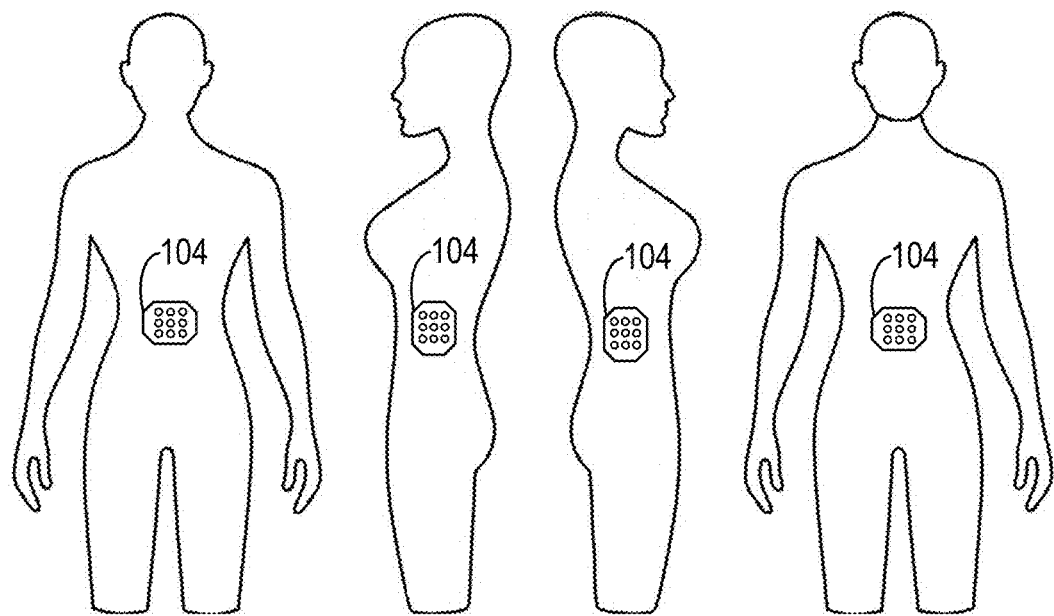
FIG. 4B shows transducer arrays placed on a patient's abdomen.
Figure 5A:
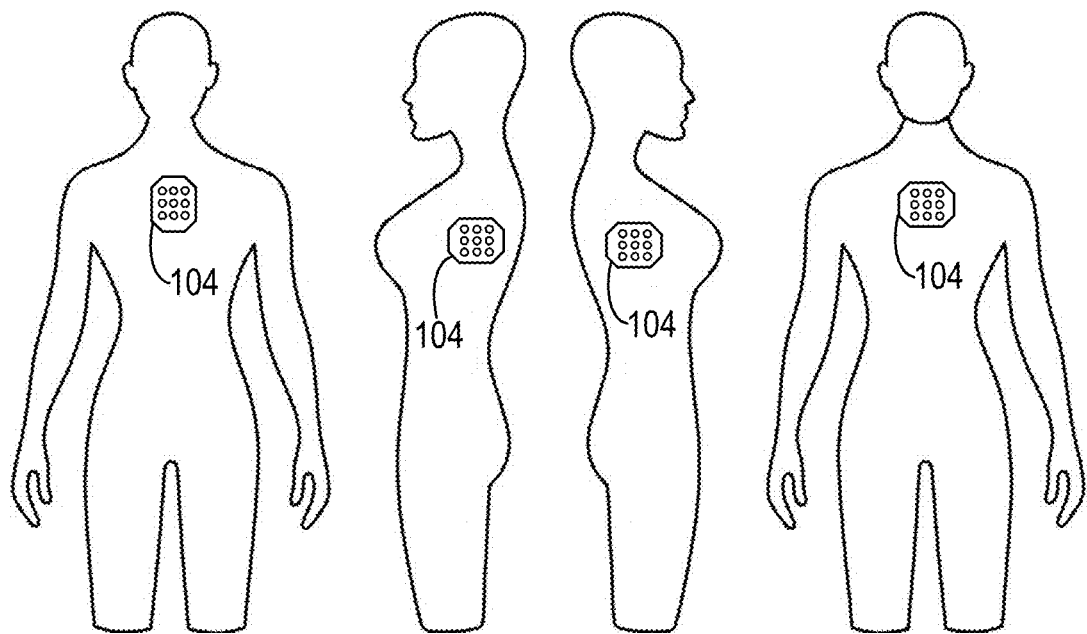
FIG. 5A, the transducer arrays placed on a patient's torso.
Figure 5B:
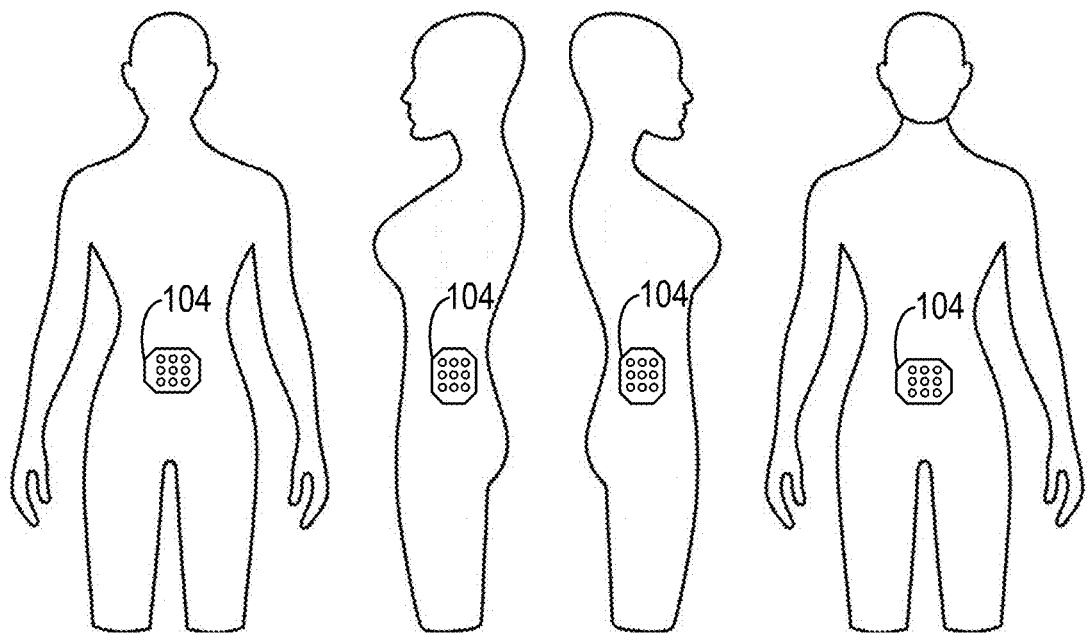
FIG. 5B shows transducer arrays placed on a patient's pelvis

As shown in FIG. 4A, the transducer arrays 104 may be placed on a patient's head. As shown in FIG. 4B, the transducer arrays 104 may be placed on a patient's abdomen. As shown in FIG. 5A, the transducer arrays 104 may be placed on a patient's torso. As shown in FIG. 5B, the transducer arrays 104 may be placed on a patient's pelvis. Placement of the transducer arrays 104 on other portions of a patient's body (e.g., arm, leg, etc.) are specifically contemplated.

Figure 6:
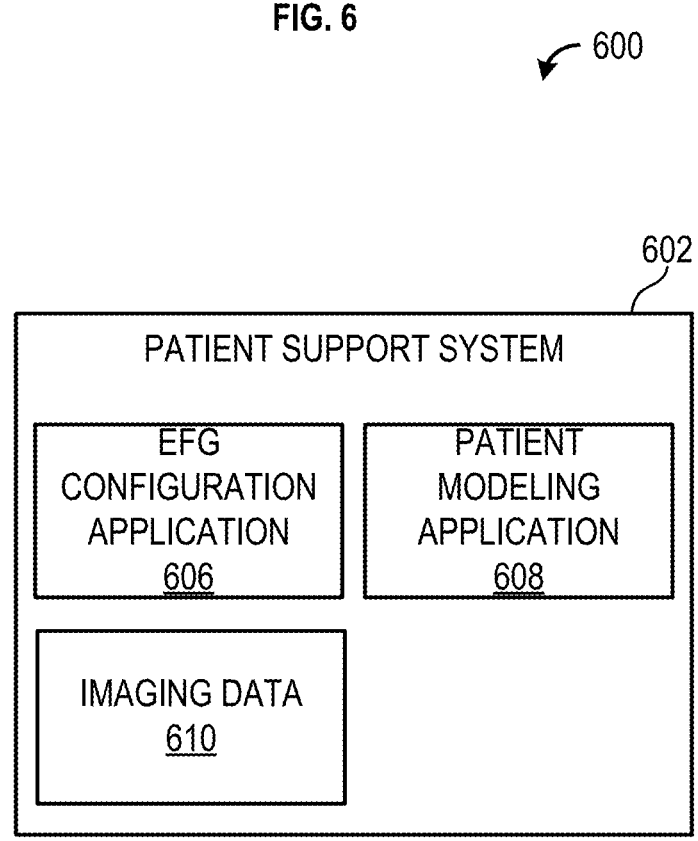
FIG. 6 is a block diagram depicting an electric field generator and a patient support system.

FIG. 6 is a block diagram depicting non-limiting examples of a system 600 comprising a patient support system 602. The patient support system 602 can comprise one or multiple computers configured to operate and/or store an electric field generator (EFG) configuration application 606, a patient modeling application 608, and/or imaging data 610. The patient support system 602 can comprise, for example, a computing device. The patient support system 602 can comprise, for example, a laptop computer, a desktop computer, a mobile phone (e.g., a smartphone), a tablet, and the like.

The patient modeling application 608 may be configured to generate a three dimensional model of a portion of a body of a patient (e.g., a patient model) according to the imaging data 610. The imaging data 610 may comprise any type of visual data, for example, single-photon emission computed tomography (SPECT) image data, x-ray computed tomography (x-ray CT) data, magnetic resonance imaging (MRI) data, positron emission tomography (PET) data, data that can be captured by an optical instrument (e.g., a photographic camera, a charge-coupled device (CCD) camera, an infrared camera, etc.), and the like. In certain implementations, image data may include 3D data obtained from or generated by a 3D scanner (e.g., point cloud data). The patient modeling application 608 may also be configured to generate a three-dimensional array layout map based on the patient model and one or more electric field simulations.

To properly optimize array placement on a portion of a patient's body, the imaging data 610, such as MRI imaging data, may be analyzed by the patient modeling application 608 to identify a region of interest that comprises a tumor. In the context of a patient's head, to characterize how electric fields behave and distribute within the human head, modeling frameworks based on anatomical head models using Finite Element Method (FEM) simulations may be used. These simulations yield realistic head models based on magnetic resonance imaging (MRI) measurements and compartmentalize tissue types such as skull, white matter, gray matter, and cerebrospinal fluid (CSF) within the head. Each tissue type may be assigned dielectric properties for relative conductivity and permittivity, and simulations may be run whereby different transducer array configurations are applied to the surface of the model to understand how an externally applied electric field, of preset frequency, will distribute throughout any portion of a patient's body, for example, the brain. The results of these simulations, employing paired array configurations, a constant current, and a preset frequency of 200 kHz, have demonstrated that electric field distributions are relatively non-uniform throughout the brain and that electric field intensities exceeding 1 V/cm are generated in most tissue compartments except CSF. These results are obtained assuming total currents with a peak-to-peak value of 1800 milliamperes (mA) at the transducer array-scalp interface. This threshold of electric field intensity is sufficient to arrest cellular proliferation in glioblastoma cell lines.

Additionally, by manipulating the configuration of paired transducer arrays, it is possible to achieve an almost tripling of electric field intensity to a particular region of the brain as shown in FIG. 7A. FIG. 7A illustrates electric field magnitude and distribution (in V/cm) shown in the coronal view from a finite element method simulation model. This simulation employs a left-right paired transducer array configuration.

Based on Ohm's law, Maxwell's equations in matter, and Coulomb's law, for TTFields, the electric field is inversely related to conductivity ($\sigma$), permittivity ($\varepsilon$), and distance from electrical source ($d_e$), respectively. As shown in FIGS. 7B-D, a close inspection of simulation results suggests that the TTFields are larger when the tissue is in the proximity of the cerebrospinal fluid (CSF).

FIG. 7B shows an example head MRI T1 with gadolinium of a GBM patient who underwent TTField treatment. FIG. 7C shows an example segmentation of the patient's MRI into tissues with different electrical properties. FIG. 7D shows TTfields spatial distribution computed with a finite element method, as described herein. Note that the TTFields are increased in the vicinity of cerebrospinal fluid (arrow). Moreover, TTFields are larger in tissues that are closer to the dashed line between the centers of TA pairs.

A possible explanation for this observation is that electrons are accumulated on the CSF's boundary since of its high conductivity, therefore, increasing the electric potential in these zones. The shortest distance of a voxel from a voxel of CSF is denoted as $d_c$. Another observation is that the TTFields are larger in tissues that are closer to the imaginary line between the centers of TA pairs (FIG. 7B). This observation is in line with a generalization of Coulomb's law to finite parallel plates in homogenous matter. The distance between a voxel and the line along TA centers is denoted dl. The conductivity and permittivity are expected to have a linear relation with the electric field, and the distance is polynomial to the electric field.

Given patient's head MRI the above key parameters were extracted as follows. At first, we have segmented the head into eight tissues (FIG. 7C): 1) skin and muscle (as one tissue); 2) skull; 3) CSF; 4) white matter; 5) grey matter; 6) tumor—enhancing; 7) tumor—necrotic, and; 8) tumor resection cavity. The segmentation of the tumor was performed semi-automatically using region growing and active contours methods. The segmentation of the head tissues (1-5) was performed automatically with a custom atlas-based method. The conductivity and permittivity of the different tissues were determined. The distances of each voxel from an electrical source, CSF and the line along TA centers were efficiently computed.

Figures 8A, 8B:
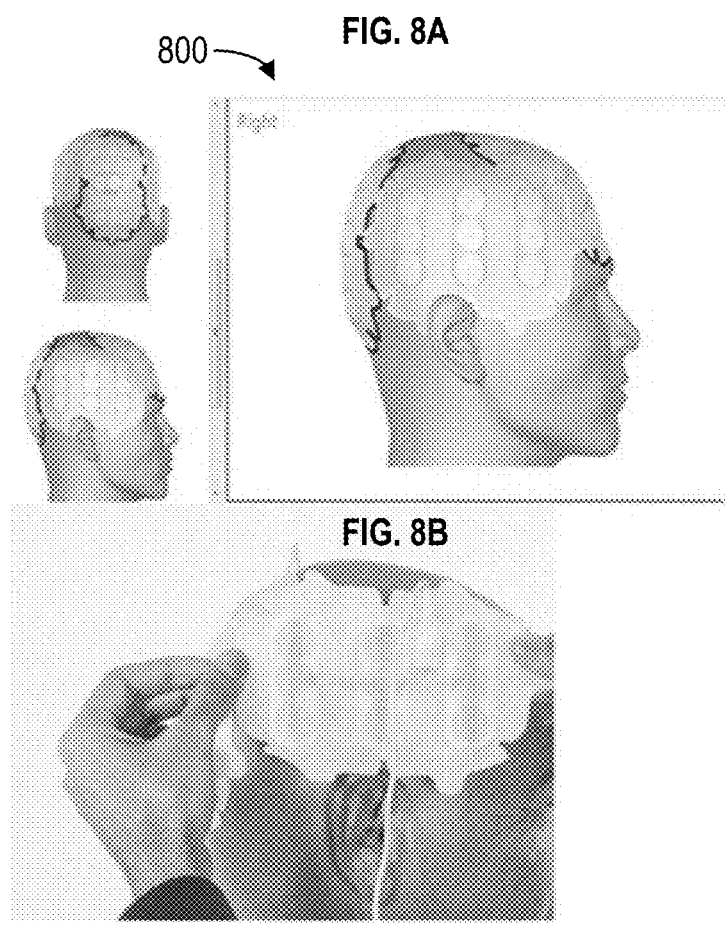
FIG. 8A shows a three-dimensional array layout map 800.
FIG. 8B shows placement of transducer arrays on the scalp of a patient.

In an aspect, the patient modeling application 608 may be configured to determine a desired (e.g., optimal) transducer array layout for a patient based on the location and extent of the tumor. For example, initial morphometric head size measurements may be determined from the T1 sequences of a brain MRI, using axial and coronal views. Postcontrast axial and coronal MRI slices may be selected to demonstrate the maximal diameter of enhancing lesions. Employing measures of head size and distances from predetermined fiducial markers to tumor margins, varying permutations, and combinations of paired array layouts may be assessed to generate the configuration which delivers maximal electric field intensity to the tumor site. As shown in FIG. 8A, the output may be a three-dimensional array layout map 800. The three-dimensional array layout map 800 may be used by the patient and/or caregiver in arranging arrays on the scalp during the normal course of TTFields therapy as shown in FIG. 8B.

In an aspect, the patient modeling application 608 can be configured to determine the three-dimensional array layout map for a patient. MRI measurements of the portion of the patient that is to receive the transducer arrays may be determined. By way of example, the MRI measurements may be received via a standard Digital Imaging and Communications in Medicine (DICOM) viewer. MRI measurement determination may be performed automatically, for example by way of artificial intelligence techniques, or may be performed manually, for example, by way of a physician.

Figure 9A:
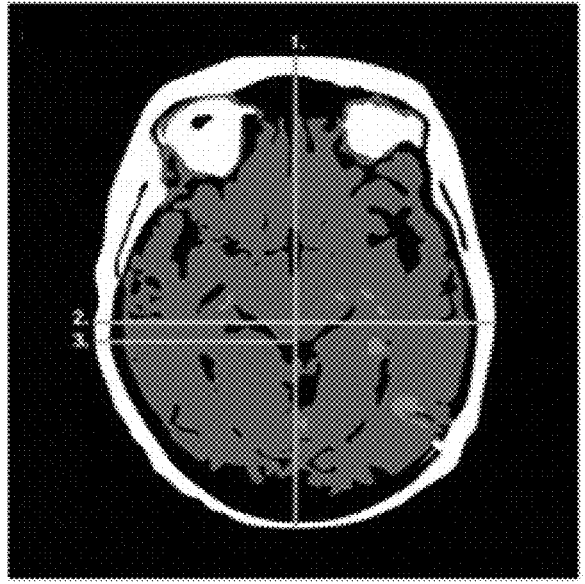
FIG. 9A shows an axial T1 sequence slice containing most apical image, including orbits used to measure head size.
Figure 9B:
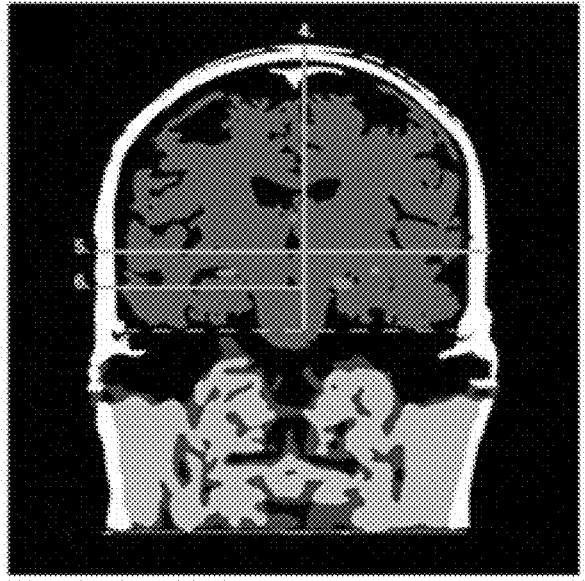
FIG. 9B shows a coronal T1 sequence slice selecting image at level of ear canal used to measure head size.
Figure 9C:
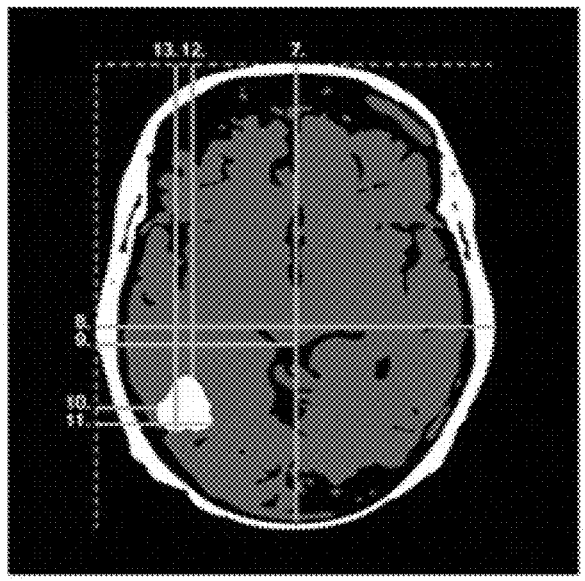
FIG. 9C shows a postcontrast T1 axial image shows maximal enhancing tumor diameter used to measure tumor location.
Figure 9D:
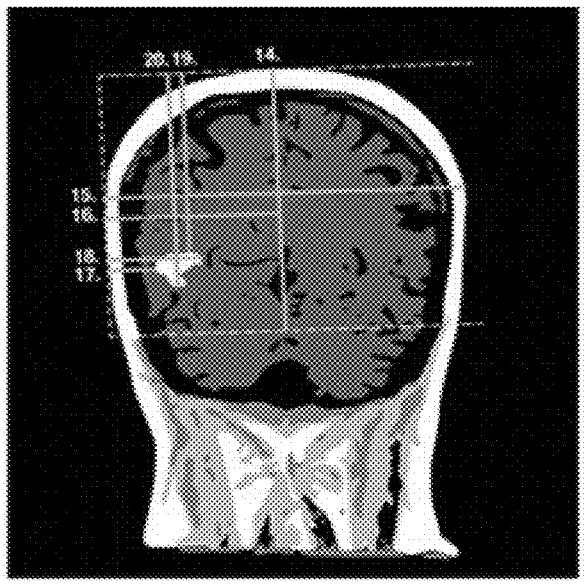
FIG. 9D shows a postcontrast T1 coronal image shows maximal enhancing tumor diameter used to measure tumor location.

Manual MRI measurement determination may comprise receiving and/or providing MRI data via a DICOM viewer. The MRI data may comprise scans of the portion of the patient that contains a tumor. By way of example, in the context of the head of a patient, the MRI data may comprise scans of the head that comprise one or more of a right frontotemporal tumor, a right parieto-temporal tumor, a left frontotemporal tumor, a left parieto-occipital tumor, and/or a multi-focal midline tumor. FIG. 9A, FIG. 9B, FIG. 9C, and FIG. 9D show example MRI data showing scans of the head of a patient. FIG. 9A shows an axial T1 sequence slice containing the most apical image, including orbits used to measure head size. FIG. 9B shows a coronal T1 sequence slice selecting image at level of ear canal used to measure head size. FIG. 9C shows a postcontrast T1 axial image shows maximal enhancing tumor diameter used to measure tumor location. FIG. 9D shows a postcontrast T1 coronal image shows maximal enhancing tumor diameter used to measure tumor location. MRI measurements may commence from fiducial markers at the outer margin of the scalp and extend tangentially from a right-, anterior-, superior origin. Morphometric head size may be estimated from the axial T1 MRI sequence selecting the most apical image which still included the orbits (or the image directly above the superior edge of the orbits)

In an aspect, the MRI measurements may comprise, for example, one or more head size measurements and/or tumor measurements. In an aspect, one or more MRI measurements may be rounded to the nearest millimeter and may be provided to a transducer array placement module (e.g., software) for analysis. The MRI measurements may then be used to generate the three-dimensional array layout map (e.g., three-dimensional array layout map 800).

The MRI measurements may comprise one or more head size measurements such as: a maximal anteroposterior (A-P) head size, commencing measurement from the outer margin of the scalp; a maximal width of the head perpendicular to the A-P measurement: the right to left lateral distance; and/or a distance from the far most right margin of the scalp to the anatomical midline.

The MRI measurements may comprise one or more head size measurements such as coronal view head size measurements. Coronal view head size measurements may be obtained on the T1 MRI sequence selecting the image at the level of the ear canal (FIG. 9B). The coronal view head size measurements may comprise one or more of: a vertical measurement from the apex of the scalp to an orthogonal line delineating the inferior margin of the temporal lobes; a maximal right to left lateral head width; and/or a distance from the far right margin of the scalp to the anatomical midline.

The MRI measurements may comprise one or more tumor measurements, such as tumor location measurements. The tumor location measurements may be made using T1 postcontrast MRI sequences, firstly on the axial image demonstrating maximal enhancing tumor diameter (FIG. 9C). The tumor location measurements may comprise one or more of: a maximal A-P head size, excluding the nose; a maximal right to left lateral diameter, measured perpendicular to the A-P distance; a distance from the right margin of the scalp to the anatomical midline; a distance from the right margin of the scalp to the closest tumor margin, measured parallel to the right-left lateral distance and perpendicular to the A-P measurement; a distance from the right margin of the scalp to the farthest tumor margin, measured parallel to the right-left lateral distance, perpendicular to the A-P measurement; a distance from the front of the head, measured parallel to the A-P measurement, to the closest tumor margin; and/or a distance from the front of the head, measured parallel to the A-P measurement, to the farthest tumor margin.

The one or more tumor measurements may comprise coronal view tumor measurements. The coronal view tumor measurements may comprise identifying the postcontrast T1 MRI slice featuring the maximal diameter of tumor enhancement (FIG. 9D). The coronal view tumor measurements may comprise one or more of: a maximal distance from the apex of the scalp to the inferior margin of the cerebrum. In anterior slices, this would be demarcated by a horizontal line drawn at the inferior margin of the frontal or temporal lobes, and posteriorly, it would extend to the lowest level of visible tentorium; a maximal right to left lateral head width; a distance from the right margin of the scalp to the anatomical midline; a distance from the right margin of the scalp to the closest tumor margin, measured parallel to the right-left lateral distance; a distance from the right margin of the scalp to the farthest tumor margin, measured parallel to the right-left lateral distance; a distance from the apex of the head to the closest tumor margin, measured parallel to the superior apex to inferior cerebrum line; and/or a distance from the apex of the head to the farthest tumor margin, measured parallel to the superior apex to inferior cerebrum line.

Other MRI measurements may be used, particularly when the tumor is present in another portion of the patient's body.

The MRI measurements may be used by the patient modeling application 608 to generate a patient model. The patient model may then be used to determine the three-dimensional array layout map (e.g., three-dimensional array layout map 800). Continuing the example of a tumor within the head of a patient, a healthy head model may be generated which serves as a deformable template from which patient models can be created. When creating a patient model, the tumor may be segmented from the patient's MRI data (e.g., the one or more MRI measurements). Segmenting the MRI data identifies the tissue type in each voxel, and electric properties may be assigned to each tissue type based on empirical data. Table 1 shows standard electrical properties of tissues that may be used in simulations. The region of the tumor in the patient MRI data may be masked, and non-rigid registration algorithms may be used to register the remaining regions of the patient head on to a 3D discrete image representing the deformable template of the healthy head model. This process yields a non-rigid transformation that maps the healthy portion of the patient's head into the template space, as well as the inverse transformation that maps the template into the patient space. The inverse transformation is applied to the 3D deformable template to yield an approximation of the patient's head in the absence of a tumor. Finally, the tumor (referred to as a region-of-interest (ROI)) is planted back into the deformed template to yield the full patient model. The patient model may be a digital representation in three-dimensional space of the portion of the patient's body, including internal structures, such as tissues, organs, tumors, etc.

TABLE 1

| Tissue Type | Conductivity, S/m | Relative Permittivity |
| --- | --- | --- |
| Scalp | 0.3 | 5000 |
| Skull | 0.08 | 200 |
| Cerebrospinal fluid | 1.79 | 110 |
| Gray matter | 0.25 | 3000 |
| White matter | 0.12 | 2000 |
| Enhancing tumor | 0.24 | 2000 |
| Enhancing nontumor | 0.36 | 1170 |
| Resection cavity | 1.79 | 110 |

TABLE 1-continued

| Tissue Type | Conductivity, S/m | Relative Permittivity |
|---|---|---|
| Necrotic tumor | 1 | 110 |
| Hematoma | 0.3 | 2000 |
| Ischemia | 0.18 | 2500 |
| Atrophy | 1 | 110 |
| Air | 0 | 0 |

Figure 10:
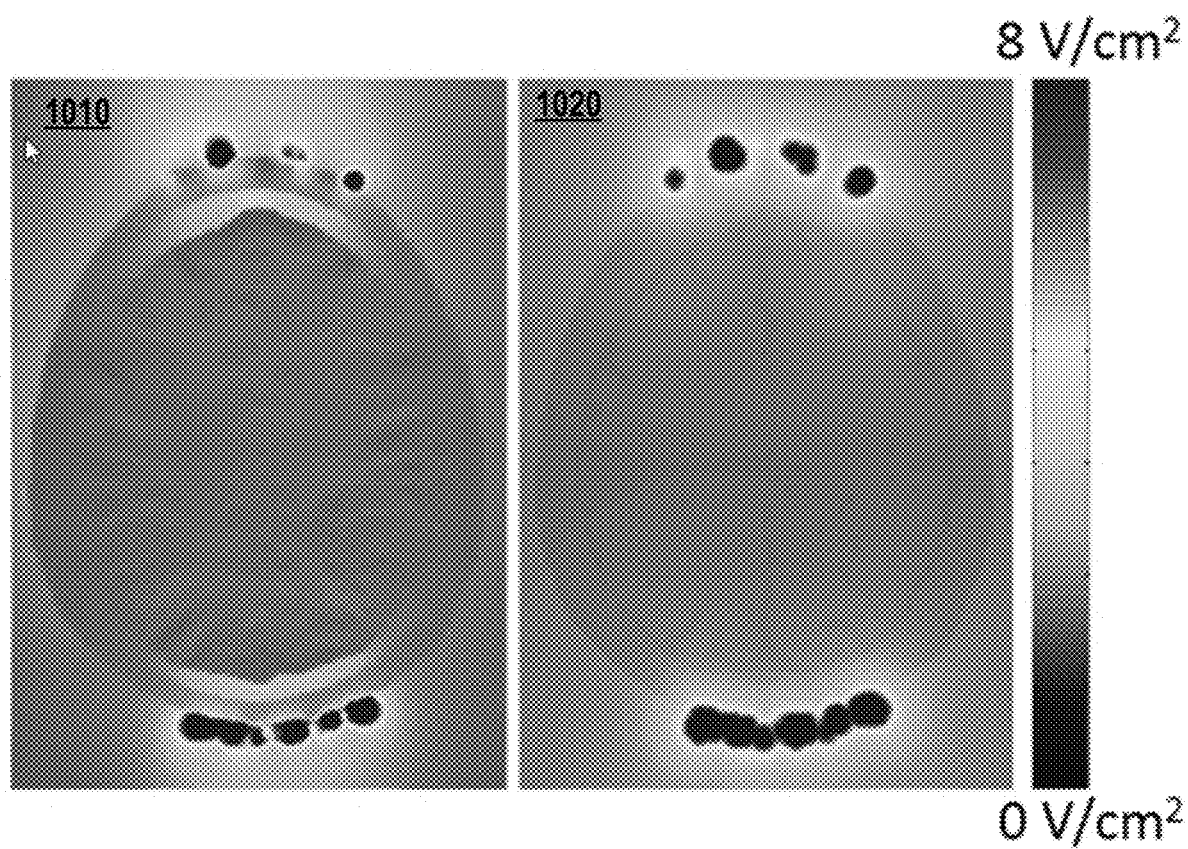
FIG. 10 absolute values of approximated electric field distributions using different methods.

In some instances, the patient modeling application 608 may use artificial intelligence and/or machine learning to determine the three-dimensional transducer array layout map for a patient. For example, features that are related to the electric field distribution may be extracted from the patient MRI. Extracted features may be incorporated in a compact model to quickly estimate, predict, and/or determine an electric field and/or electric field distributions for transducer arrays by providing a precomputed mapping from the MRI features to electric field values. Modeling may be based on a linear equation or may involve a complex machine learning model. For example, a model may be tested based on a dataset determined from a patient that underwent TTFields therapy for the management of Glioblastoma Multiforme (GBM). A dataset may be based on data from a three-dimensional (3D) MRI image of the patient's head (or any other region of the patient's body) where voxels are labeled to indicate segmentation of a tumor and different tissue types, such as: combined skin and muscle tissue, skull/bone, cerebrospinal fluid, gray matter, and white matter. Unlabeled voxels of the 3D image may be considered air. Given that electric field strength is inversely related to conductivity, permittivity, distance from an electric source, and distance from a conductive material, the following modeling equation may be used:

$$|E| \sim a_1 c^{-1} + a_2 p^{-1} + a_3 d_{TA}^{-1} + a_4 d_{TA}^{-2} + a_5 d_{conductor}^{-1} + a_6, \quad \text{Equation 1:}$$

where c denotes conductivity, p denotes permittivity, $d_{TA}$ denotes the distance to closest transducer array and $d_{conductor}$ denotes the distance to the closest conductor. The coefficients at represent the model and are computed once. Equation 1 represents a simple model that may be solved quickly, for example using a differential equation solver, using linear approximation, and/or the like. A differential equation solver may be used to solve Equation 1. For example, using a differential equation solver, the approximate time of computation is three (3) hours. A threshold may be applied on the resulted electric field determined by the differential equation solver to create a binary image that represents the location of the transducer arrays. It should be noted that in some instances, the dataset used for the model may include data from each transducer arrays. To approximate the electric field using the Equation 1, each voxel in the 3D MRI image may be associated with conductivity and permittivity values according to a tissue type associated with the voxel. The distances between closest transducers and closest cerebrospinal fluid may be computed at each voxel. The coefficients $a_i$ of Equation 1 may be computed to minimize the least square error. Computation of Equation 1 may be applied to each voxel of the 3D MRI image to create a volume of the approximated electric field. FIG. 10 illustrates computed electric field absolute values. 1010 illustrates electric field absolute values computed with the differential equations solver, where the approximate time of computation was three (3) hours. 1020 illustrates electric field absolute values computed using fast linear approximation, where the approximate time of computation was four (4) minutes.

Comparing the results of quickly approximated electric fields using modeling to fully computed electric fields reveals that the average difference between the estimated and the fully computed fields is 0.56 V/cm2 (SD=2.01 V/cm2), with a Pearson's correlation coefficient between estimation and full computation being 0.74 (p<0.05), which indicates that that the electric field may be approximated with fast computation. Machine learning may be used to determine more complex models that yield improved estimations with less time.

A machine learning model may be trained according to multiple datasets (or a large dataset) created from features extracted from 3D MRI images from a wide variety of patients, such as patients that underwent TTFields therapy for the management of Glioblastoma Multiforme (GBM). Features extracted from each image may include a patient's head where voxels are labeled to indicate segmentation of a tumor and different tissue types, such as: combined skin and muscle tissue, skull/bone, cerebrospinal fluid, gray matter, and white matter. Unlabeled voxels of the 3D image may be considered air. It should be noted that the datasets (or large dataset) may be changed, modified, and/or the like to include any data relevant to computing electric fields for transducer array layouts.

Figure 11:
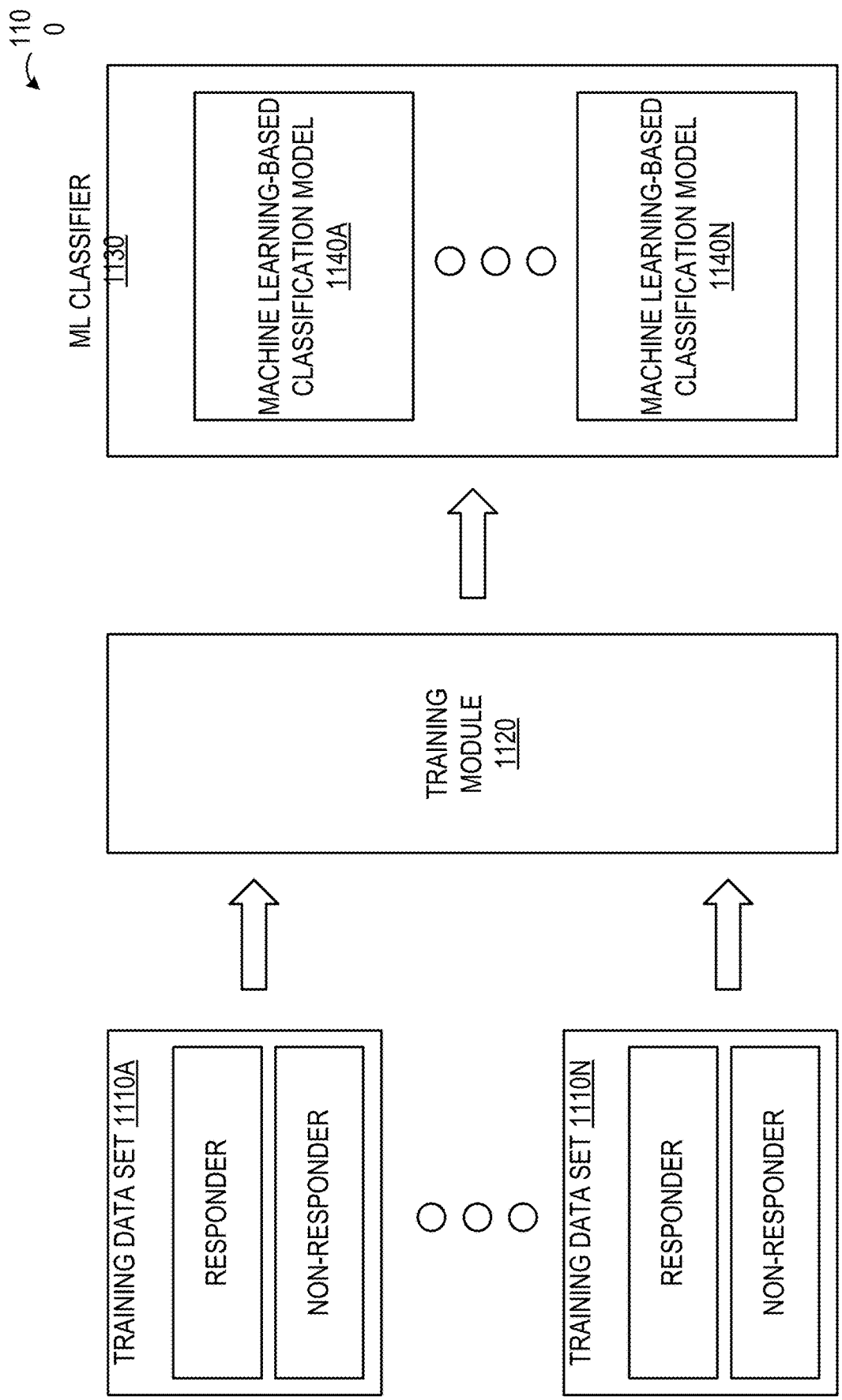
FIG. 11 shows an example machine learning system.

As shown in FIG. 11, a system 1100 may use machine learning techniques to train, based on an analysis of one or more training data sets 1110A-110N by a training module 1120, at least one machine learning-based classifier 1130 that is configured to classify features extracted from 3D MRI images comprising a plurality of voxels. The machine learning-based classifier 1130 may classify features extracted from 3D MRI images to enable fast approximation of electric field distribution based on a predictive model.

The one or more training data sets 1110A-1110N may comprise labeled baseline tissue type, electric field distributions, transducer array positions that induce therapeutic tumor treating fields, and/or the like from a large volume of patient 3D MRI images. The labeled baseline data may be associated with patients treated for glioblastoma (GBM), or any other cancer. In some instances, the labeled dataset may include features extracted from 3D MRI images of other portions of patients' anatomy, from different tumor tissues, from transducer arrays configured with various materials, and/or the like. In some instances, the labeled baseline data may comprise labeled baseline data from patients before, during, and after administering TTFields treatment. The labeled baseline data may include any number of feature sets (labeled data that identify extracted features). A feature set may be based on segmentation of a tumor, different tissue types (e.g., combined skin and muscle tissue, skull/bone, cerebrospinal fluid, gray matter, and white matter, etc.), or any other feature relevant to (e.g., that may affect, etc.) an electric field and/or electric field distributions for transducer arrays. For example, each voxel of a 3D MRI image may be labeled with a tissue type and labeled with an electric field strength distribution value (V cm-1) derived from a simulated application of an alternating electric field from a pair of transducer arrays to a portion of a patient.

The labeled baseline data may be stored in one or more databases. Data for each patient may be randomly assigned to a training data set or a testing data set. In some implementations, the assignment of data to a training data set or a testing data set may not be completely random. In this case, one or more criteria may be used during the assignment, such as ensuring that similar numbers of patients with varying degrees of cancer (e.g., benign, malignant, etc.), different transducer array layouts, different transducer configuration material, and/or the like may be used in each of the training and testing data sets. In general, any suitable method may be used to assign the data to the training or testing data sets.

The training module 1120 may train the machine learning-based classifier 1130 by extracting a feature set from the labeled baseline data according to one or more feature selection techniques. In some instances, the training module 1120 may further define the feature set obtained from the labeled baseline data by applying one or more feature selection techniques to the labeled baseline data in the one or more training data sets 1110A-1110N. The training module 1120 may extract a feature set from the training data sets 1110A-1110N in a variety of ways. The training module 1120 may perform feature extraction multiple times, each time using a different feature-extraction technique. In some instances, the feature sets generated using the different techniques may each be used to generate different machine learning-based classification models 1140. In an embodiment, the feature set with the highest quality metrics may be selected for use in training. The training module 1120 may use the feature set(s) to build one or more machine learning-based classification models 1140A-1140N that are configured for fast approximation of electric field distribution.

In some instances, the training data sets 110A-110N and/or the labeled baseline data may be analyzed to determine any dependencies, associations, and/or correlations between transducer array positions, tissue types, and electric field distribution in the training data sets 1110A-1110N and/or the labeled baseline data. The term "feature," as used herein, may refer to any characteristic of an item of data that may be used to determine whether the item of data falls within one or more specific categories. By way of example, the features described herein may comprise transducer array characteristics (e.g., material characteristics, positioning rules and characteristics, tissue types, and related electric/dielectric properties (e.g., conductivity, permittivity, etc.), electric field distributions, and/or the like.

In some instances, a feature selection technique may comprise one or more feature selection rules. The one or more feature selection rules may comprise an electric field distribution rule. The electric field distribution rule may comprise determining which features in the labeled baseline data appear over a threshold number of times in the labeled baseline data and identifying those features that satisfy the threshold as candidate features. For example, any feature that appears greater than or equal to 2 times in the labeled baseline data may be considered as candidate features. Any features appearing less than 2 times may be excluded from consideration as a feature. In some instances, a single feature selection rule may be applied to select features or multiple feature selection rules may be applied to select features. In some instances, the feature selection rules may be applied in a cascading fashion, with the feature selection rules being applied in a specific order and applied to the results of the previous rule. For example, the electric field distribution rule may be applied to the labeled baseline data to generate electric field distributions based on a transducer array location. A final list of candidate genes may be analyzed according to an additional feature.

In some instances, a fast approximation of electric field distribution may be based on a wrapper method. A wrapper method may be configured to use a subset of features and train a machine learning model using the subset of features. Based on the inferences drawn from a previous model, features may be added and/or deleted from the subset. Wrapper methods include, for example, forward feature selection, backward feature elimination, recursive feature elimination, combinations thereof, and the like. In some instances, forward feature selection may be used to identify one or more candidate electric field distributions. Forward feature selection is an iterative method that begins with no feature in the machine learning model. In each iteration, the feature which best improves the model is added until the addition of a new variable does not improve the performance of the machine learning model. In an embodiment, backward elimination may be used to identify one or more candidate electric field distributions. Backward elimination is an iterative method that begins with all features in the machine learning model. In each iteration, the least significant feature is removed until no improvement is observed on the removal of features. In an embodiment, recursive feature elimination may be used to identify one or more candidate electric field distributions. Recursive feature elimination is a greedy optimization algorithm which aims to find the best performing feature subset. Recursive feature elimination repeatedly creates models and keeps aside the best or the worst performing feature at each iteration. Recursive feature elimination constructs the next model with the features remaining until all the features are exhausted. Recursive feature elimination then ranks the features based on the order of their elimination.

In some instances, one or more candidate electric field distributions (approximations) may be selected according to an embedded method. Embedded methods combine the qualities of filter and wrapper methods. Embedded methods include, for example, Least Absolute Shrinkage and Selection Operator (LASSO) and ridge regression which implement penalization functions to reduce overfitting. For example, LASSO regression performs L1 regularization which adds a penalty equivalent to the absolute value of the magnitude of coefficients and ridge regression performs L2 regularization which adds a penalty equivalent to the square of the magnitude of coefficients.

After training module 1120 has generated a feature set(s), the training module 1120 may generate a machine learning-based predictive model 1140 based on the feature set(s). The machine learning-based predictive model may refer to a complex mathematical model for data classification that is generated using machine-learning techniques. In one example, this machine learning-based classifier may include a map of support vectors that represent boundary features. By way of example, boundary features may be selected from, and/or represent the highest-ranked features in, a feature set.

In an embodiment, the training module 1120 may use the feature sets extracted from the training data sets 1110A-1110N and/or the labeled baseline data to build a machine learning-based classification model 1140A-1140N to approximate electric field distributions for a variety of transducer array layouts. In some examples, the machine learning-based classification models 1140A-1140N may be combined into a single machine learning-based classification model 1140. Similarly, the machine learning-based classifier 1130 may represent a single classifier containing a single or a plurality of machine learning-based classification models 1140 and/or multiple classifiers containing a single or a plurality of machine learning-based classification models 1140. Also, in some embodiments, the machine learning-based classifier 130 may include each of the training data sets 1110A-1110N and/or each feature set extracted from the training data sets 1110A-810N and/or extracted from the labeled baseline data.

The extracted features from the 3D MRI images may be combined in a classification model trained using a machine learning approach such as discriminant analysis; decision tree; a nearest neighbor (NN) algorithm (e.g., k-NN models, replicator NN models, etc.); statistical algorithm (e.g., Bayesian networks, etc.); clustering algorithm (e.g., k-means, mean-shift, etc.); neural networks (e.g., reservoir networks, artificial neural networks, etc.); support vector machines (SVMs); logistic regression algorithms; linear regression algorithms; Markov models or chains; principal component analysis (PCA) (e.g., for linear models); multi-layer perceptron (MLP) ANNs (e.g., for non-linear models); replicating reservoir networks (e.g., for non-linear models, typically for time series); random forest classification; a combination thereof and/or the like. The resulting machine learning-based classifier 1130 may comprise a decision rule or a mapping that uses transducer array layout for a candidate electric field distribution The transducer array layout and the machine learning-based classifier 1130 may be used to approximate the related electric field distribution of the test samples in the test data set. In one example, the result for each test sample includes a confidence level that corresponds to a likelihood or a probability that the corresponding test sample belongs in the approximated electric field distribution. The confidence level may be a value between zero and one that represents a likelihood that the approximated electric field is consistent with a computed value. Multiple confidence levels may be provided for each test sample and each candidate (approximated) electric field distribution. A top-performing candidate electric field distribution may be determined by comparing the result obtained for each test sample with a computed electric field distribution for each test sample. In general, the top-performing candidate electric field distributions will have results that closely match the computed electric field distribution. The top-performing candidate electric field distributions may be used for fast approximation of electric field distribution.

Figure 12:
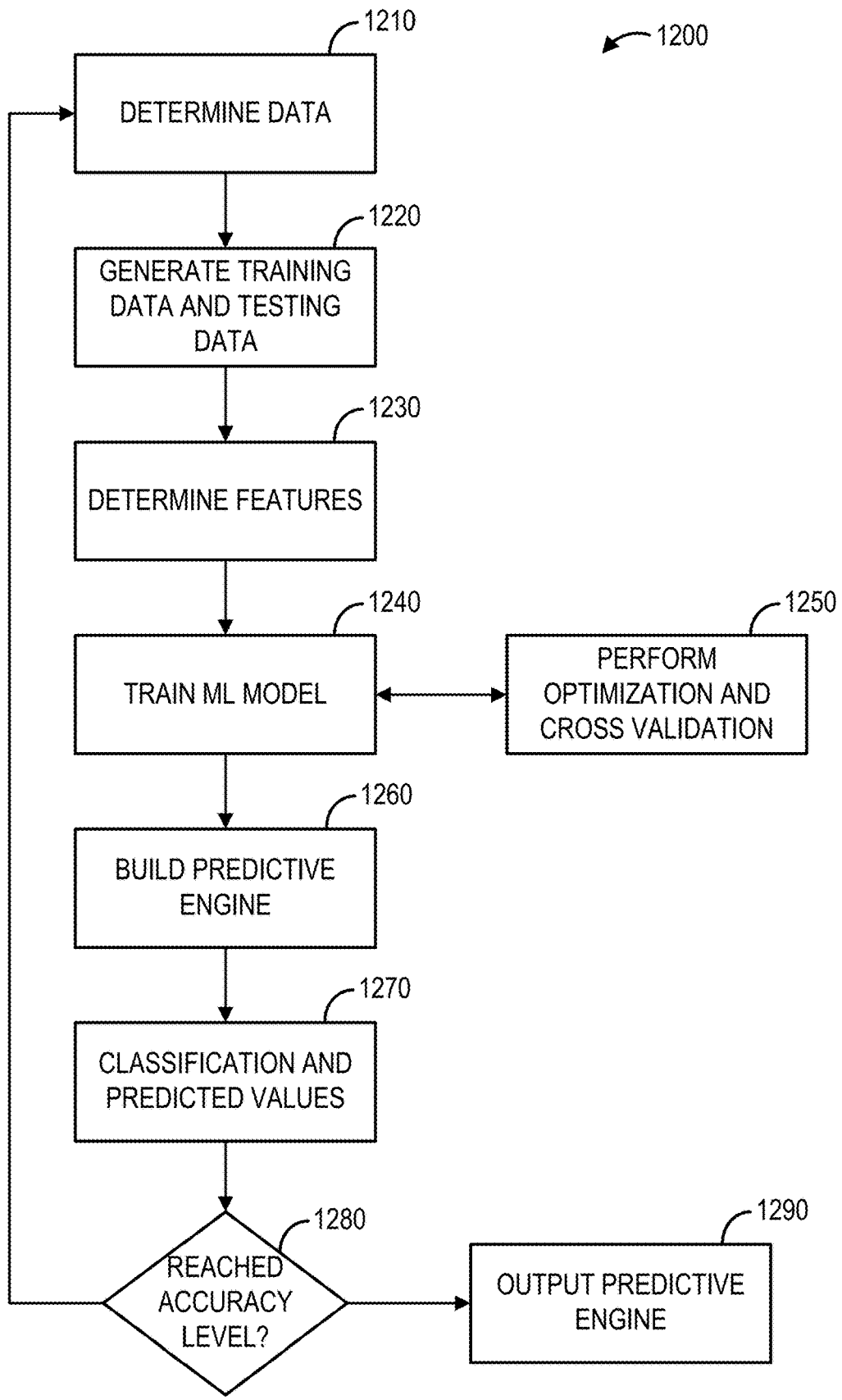
FIG. 12 shows an example machine learning method.

FIG. 12 is a flowchart illustrating an example training method 1200 for fast approximation of electric field distribution using the training module 1120. The training module 1120 can implement supervised, unsupervised, and/or semi-supervised (e.g., reinforcement-based) machine learning-based classification models 1140. The method 1200 illustrated in FIG. 12 is an example of a supervised learning method; variations of this example of training method are discussed below, however, other training methods can be analogously implemented to train unsupervised and/or semi-supervised machine learning (predictive) models.

The training method 1200 may determine (e.g., access, receive, retrieve, etc.) 3D MRI data of one or more populations of patients at 1210. The electric field distribution data may contain one or more datasets, each dataset associated with the segmentation of a tumor, different tissue types (e.g., combined skin and muscle tissue, skull/bone, cerebrospinal fluid, gray matter, and white matter, etc.), or any other feature relevant to (e.g., that may affect, etc.) an electric field and/or electric field distributions for transducer arrays. Each dataset may include labeled baseline data. Each dataset may further include labeled tumor, tissue types (e.g., combined skin and muscle tissue, skull/bone, cerebrospinal fluid, gray matter, and white matter, etc.), or any other data relevant to (e.g., that may affect, etc.) an electric field and/or electric field distributions for transducer arrays.

The training method 1200 may generate, at 1220, a training data set and a testing data set. The training data set and the testing data set may be generated by calculating and/or computing electric field distributions for transducer arrays at different positions on different areas of patients. In some instances, the training data set and the testing data set may be generated by randomly assigning electric field distribution data to either the training data set or the testing data set. In some instances, the assignment of electric field distribution data as training or test samples may not be completely random. In some instances, only the labeled baseline data for a specific feature extracted from the 3D MRI may be used to generate the training data set and the testing data set. In some instances, a majority of the labeled baseline data extracted from the 3D MRI may be used to generate the training data set. For example, 75% of the labeled baseline data extracted from the 3D MRI may be used to generate the training data set and 25% may be used to generate the testing data set. Any method or technique may be used to create the training and testing datasets.

The training method 1200 may determine (e.g., extract, select, etc.), at 1230, one or more features that can be used by, for example, a classifier label features extracted from a variety of 3D MRI images. The one or more features may comprise tumor identifiers/data (e.g., cell type, cell orientation, etc.), tissue types (e.g., combined skin and muscle tissue, skull/bone, cerebrospinal fluid, gray matter, and white matter, etc.), or any other data relevant to (e.g., that may affect, etc.) an electric field and/or electric field distributions for transducer arrays. In some instances, the training method 1200 may determine a set of training baseline features from the training data set. In some instances, the training method 1200 may determine a set of training in-treatment transducer array layouts and associated electric field distributions from the training data set. Features of 3D MRI images may be determined by any method.

The training method 1200 may train one or more machine learning models using the one or more features at 1240. In some instances, the machine learning models may be trained using supervised learning. In another embodiment, other machine learning techniques may be employed, including unsupervised learning and semi-supervised. The machine learning models trained at 1240 may be selected based on different criteria (e.g., transducer array material, applied signal strength and frequencies, etc.) and/or data available in the training data set. For example, machine learning classifiers can suffer from different degrees of bias. Accordingly, more than one machine learning model can be trained at 1240, optimized, improved, and cross-validated at 1250.

The training method 1200 may select one or more machine learning models to build a predictive model at 1260 (e.g., a machine learning classifier, a predictive model, etc.). The predictive engine may be evaluated using the testing data set. The predictive engine may analyze the testing data set and generate classification values and/or predicted values at 1270. Classification and/or prediction values may be evaluated at 1280 to determine whether such values have achieved a desired accuracy level. Performance of the predictive engine may be evaluated in a number of ways based on a number of true positives, false positives, true negatives, and/or false negatives classifications of the plurality of data points indicated by the predictive engine. For example, the false positives of the predictive engine may refer to a number of times the predictive engine incorrectly approximated an electric field distribution. Conversely, the false negatives of the predictive engine may refer to a number of times the machine learning model approximated an electric field distribution for a particular transducer array layout incorrectly, when in fact, the approximated electric field distribution matches a computed electric field distribution.

True negatives and true positives may refer to a number of times the predictive engine correctly approximated an electric field distribution. Related to these measurements are the concepts of recall and precision. Generally, recall refers to a ratio of true positives to a sum of true positives and false negatives, which quantifies a sensitivity of the predictive engine. Similarly, precision refers to a ratio of true positives a sum of true and false positives.

When such a desired accuracy level is reached, the training phase ends, and the predictive engine may be output at 1290; when the desired accuracy level is not reached, however, then a subsequent iteration of the training method 1200 may be performed starting at 1210 with variations such as, for example, considering a larger collection transducer array layout related electric field distribution data determined from a larger number of 3D MRI images.

A trained predictive model (e.g., system 1100, etc.) may use random forest regression for estimations of TTFields. Estimations of TTFields may be used to determine optimal locations for transducer arrays. Random forests are an ensemble of decision tree predictors, such that each tree is restricted by a random vector that governs the sensitivity of the tree to the input features. It has been demonstrated that regression trees facilitate effective modeling of FEM-based non-linear maps for fields of mechanical force. Moreover, they suggest that since random forests divide the dataset into groups of similar features and facilitate local group fitting, good models can be generated also when the data is heterogeneous, irregular, and of limited size.

The methods, systems, and apparatuses described herein for fast approximation of electric field distribution may use a random forest regressor. For example, a setup of 30 trees, mean squared error quality of split measure, using bootstrap and out-of-bag samples may be used to estimate regression quality on unseen samples. The number of trees may be selected by a trial-and-error process to balance accuracy and prediction-time tradeoff. The input per voxel to the regression tree may be as follows. 1) conductivity ($\sigma$); 2) permittivity ($\varepsilon$); 3) distance from closest electrical source ($d_e$); 4) distance from closest CSF ($d_c$), and; 5) distance from TAs midline (dl).

Figure 13:
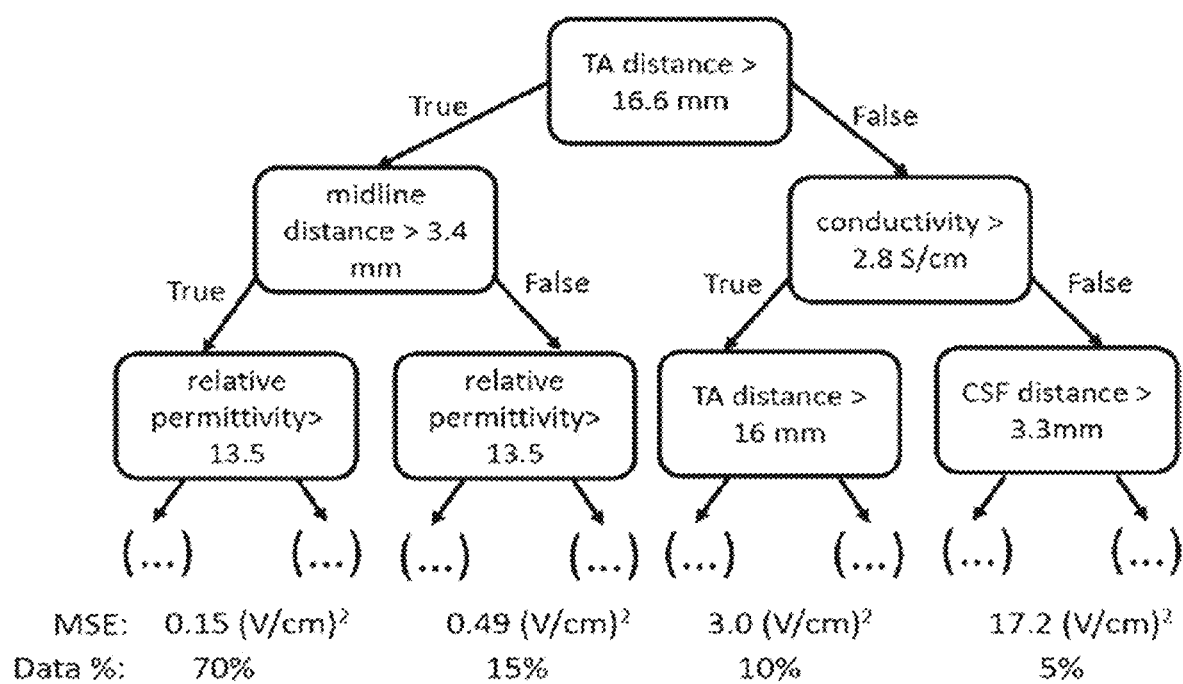
FIG. 13 shows an example decision tree.

Testing shows the relevance of the features (e.g., conductivity ($\sigma$), permittivity ($\varepsilon$), distance from the closest electrical source ($d_e$), distance from closest CSF ($d_c$), distance from TAs midline (dl), etc.) may be used for prediction in an experimental setup (as described later herein) using the mean decrease in impurity method that results with a feature's importance score in the range of 0 to 1. The distance of the closest electrical source was by far the most important feature (0.65). Distance from transducer array (TA) midline and CSF were of secondary importance (0.15 and 0.1, respectively). Conductivity and permittivity importance scores were both 0.05. FIG. 13 shows an example of a decision tree in the random forest. Notably, the mean squared error (MSE) was reduced for locations that are further from the TA. The specific tree in this example splits the data at 16.6 mm distance to TA. Indeed, larger errors were observed for the 15% of data that are within this range.

Further, testing was used to compare the random forest to a multi-linear regression. Specifically, a linear formula (Equation 2) was incorporated to estimate the TTFields.

$$|E| \sim a0 + a1\sigma^{-1} + a2\varepsilon^{-1} + a3de^{-1} + a4de^{-2} + a5d_e + a6dl \quad \text{Equation 2:}$$

The coefficients ai were computed to best fit the finite elements method output to the linear regression model.

Experimental Setup

Figures 14A, 14B, 14C:
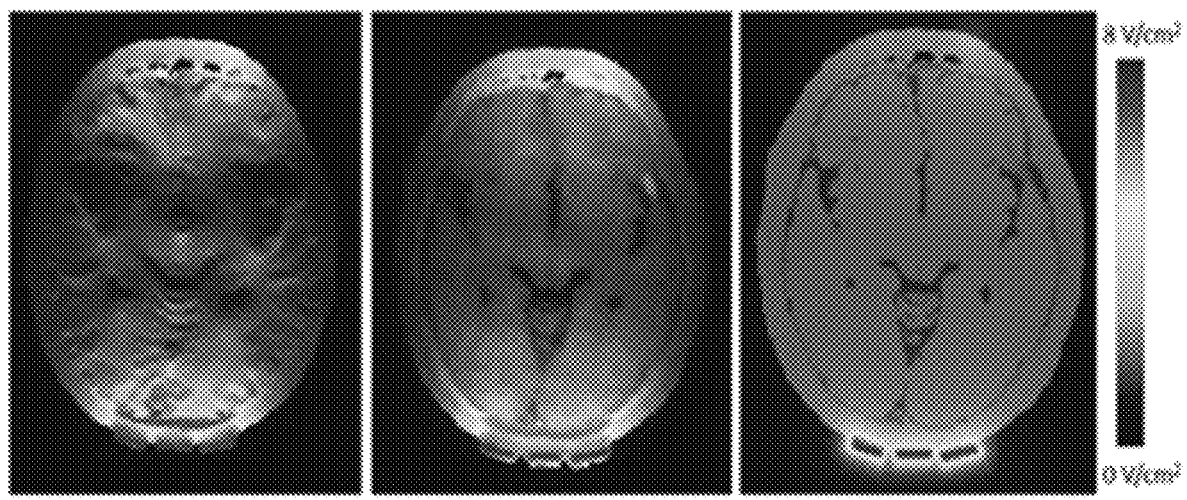
FIGS. 14A-C show example TTFields estimations.

Testing was used to validate the methods described herein using a dataset of 10 patients that underwent TTFields therapy. At first, the patients' MRIs were segmented and the head's outer surface was extracted using the marching cubes algorithm. Then, two transducer array (TA) pairs were virtually placed on the head's surface. The first pair was placed such that one TA is on the forehead and the other one is on the back of the head. In this case, the TTField direction is roughly parallel to the anterior-posterior (AP) axis. The second pair was placed such that the TAs are on opposite lateral sides of the head. In this case, the TTField direction is roughly parallel to the left-right (LR) axis of the head. For each of the 20 pairs, the absolute electric field intensity spatial distribution was determined with a finite element method. FIG. 14 shows example results. As shown in FIGS. 14A-C, an association for the electric field for each voxel in the patient's MRI was determined. The dataset was marked as a gold standard as it was verified in phantoms and associated with patients' survival. FIG. 14A shows the results of TTFields estimation that was computed by the gold standard finite-elements method. FIG. 14B shows the results of TTFields estimation that was computed by random forest regression. FIG. 14C shows the results of TTFields estimation that was computed by linear regression.

A leave-one-out approach was used for training. One test patient was excluded at a time while the 18 datasets of the rest nine patients were incorporated to train the random forest and the multilinear regression model (Equation 2).

The TTFields were predicted using random forest and multilinear regression model on the test patient data. Large parts of the image are associated with air that is not conductive. Therefore, it can bias the result of the model. To handle this situation, only a small portion of the voxels with air in the training was considered by ensuring that their number is similar to those in other segmented tissues. The training and prediction are performed per voxel independently of its neighbors.

The method may be implemented, for example, with Python 3.6 using scipy, numpy, scikit-learn, and SimpleITK packages. A 3D Slicer was used, for example, visual inspection of the results. The gold standard simulations may be computed using sim4life (Zurich Med Tech, Zurich, Switzerland) on a dedicated simulation computer (e.g., Intel i7 CPU, NVidia 1080 T1 GPU, 128 GB RAM, etc.). Patients' MRIs were T1 weighted with gadolinium with voxel spacing of 1×1×1 mm3 and incorporated the entire head.

Results

The average absolute differences between the random forest prediction and the gold standard was 0.14 V/cm (patients' SD=0.035, range 0.08-0.23 V/cm, N=20). Table 2 shows a per-patient summary of our results.

TABLE 2

| Patient # | AP Error (V/cm) | LR Error (V/cm) |
|---|---|---|
| 1 | 0.14 (0.62) | 0.23 (0.80) |
| 2 | 0.16 (0.56) | 0.19 (0.71) |
| 3 | 0.15 (0.69) | 0.17 (0.59) |
| 4 | 0.15 (0.61) | 0.18 (0.66) |
| 5 | 0.15 (0.61) | 0.15 (0.59) |
| 6 | 0.08 (0.45) | 0.08 (0.43) |
| 7 | 0.15 (0.61) | 0.14 (0.62) |
| 8 | 0.10 (0.50) | 0.11 (0.49) |
| 9 | 0.14 (0.60) | 0.14 (0.64) |
| 10 | 0.11 (0.55) | 0.13 (0.62) |

As shown in Table 2, random forest regression resulted in better accuracy in comparison to the multilinear regression. Compare the random forest average absolute differences above and the linear regression results of 0.29 V/cm (patients' SD=0.04, range 0.23-0.37 V/cm, N=20). The random forest average prediction time was 15 seconds (SD=1.5 seconds). Note that this measure is excluding the preprocessing required to extract the distance measures that typically required 30 seconds for each: TA, CSF, and midline.

Figures 15A, 15B:
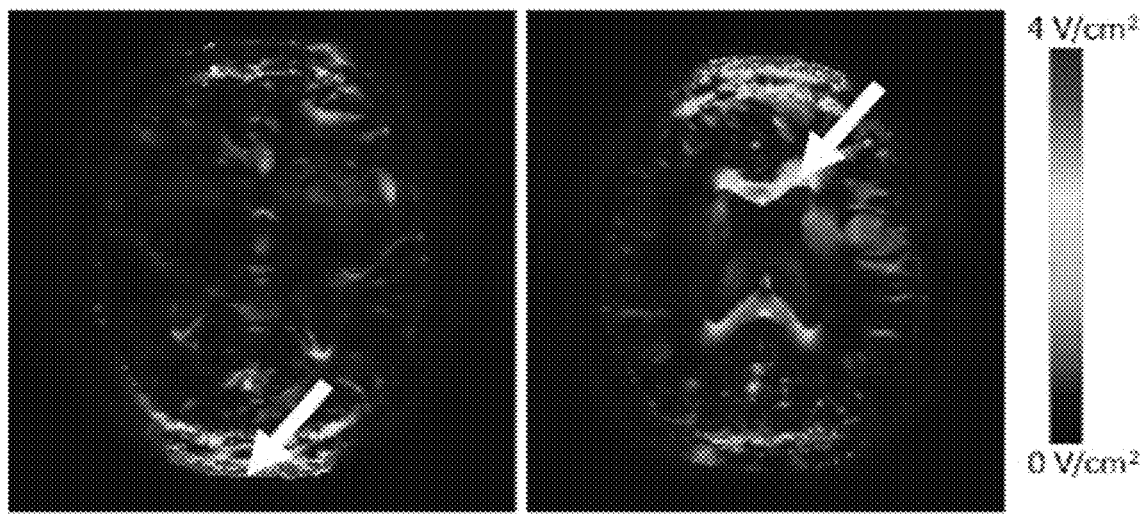
FIGS. 15A-B show example TTFields estimations.

FIGS. 14A-C shows typical electric-field spatial distributions that were computed by the gold-standard, the random forest, and the multilinear regression. FIGS. 15A-B shows typical absolute differences between the gold-standard and random-forest prediction. FIGS. 15A-B show that larger errors were observed near the transducer arrays (FIG. 15A) and near the ventricles along the main transducer array axis (FIG. 15B).

The values are very similar (<0.4 V/cm) in most locations. However, large errors (>2 V/cm) were observed in the vicinity of the TAs (FIG. 4a) and instantly outside the ventricles along the TA main axis (FIG. 15B).

As shown and described, the methods, systems, and apparatuses, described herein may be used for the fast estimation of TTFields spatial distribution. Results show that an average accuracy of 0.14 V/cm can be achieved within a short time. Compare the ~1.5 minutes computation time with the suggested random forest method to the 3-4 hours computation time using the gold standard method. Note that the computation time can be further reduced by a factor of three by the parallelization of data preparation.

Selection of optimal TA location involves the computation of average TTFields over a tumor area. Averaging is may further improve accuracy. The random forest method may also be used for TTFields estimation for optimization of TA placement.

The methods described herein may incorporate neighbor voxels and consider convolutional and recurrent neural networks. One-time distance-maps computation and fast manipulation of these maps based on the alternation of TA locations may be used to reduce overall computation time to a few seconds. The methods described herein may be used for any portion of the body of a patient undergoing TTFields treatment.

In some instances, fast approximations of electric field distributions (e.g., the output of the predictive engine at 1290, etc.) may be used to provide one or more candidate positions for a transducer array(s) placement on an area of a patient's anatomy (e.g., head, torso, etc.). For example, fast approximations of electric field distributions may be used to determine one or more electric field distribution strength values for the pair of transducer arrays at each of a plurality of positions on the patient's anatomy. The one or more candidate positions for transducer array placement may be used to determine optimal locations for transducer arrays.

Optimal locations for transducer arrays may be determined based on a patient model, fast approximations of distributed electric field strength values for the pair of transducer arrays at each of a plurality of positions, the region of interest (ROI) (e.g., tumor location, etc.) and an anatomical restriction associated with the patient's anatomy. The anatomical restriction may indicate one or more positions of a transverse plane of the ROI that should be excluded from use in determining the electric field distribution map. A plane that transverses a portion of the patient's body may be determined based on a center of the ROI.

Figure 16A:
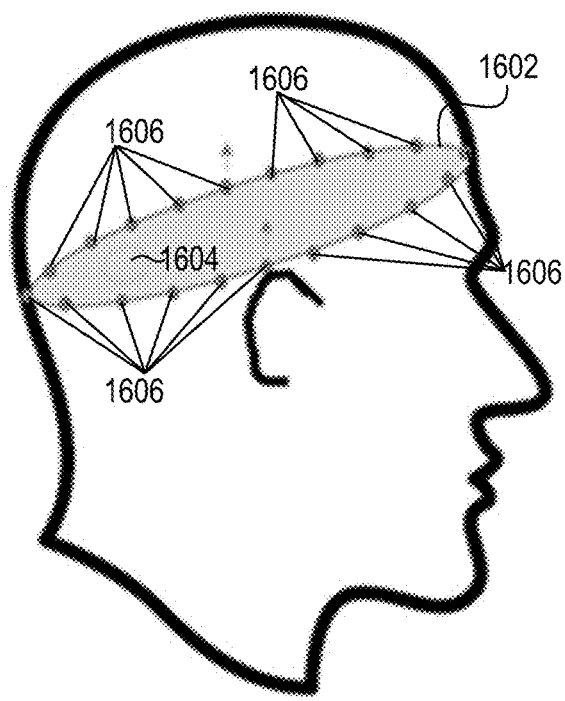
FIG. 16A shows an example transverse plan based on a center point of a tumor in a head of a patient.
Figure 16B:
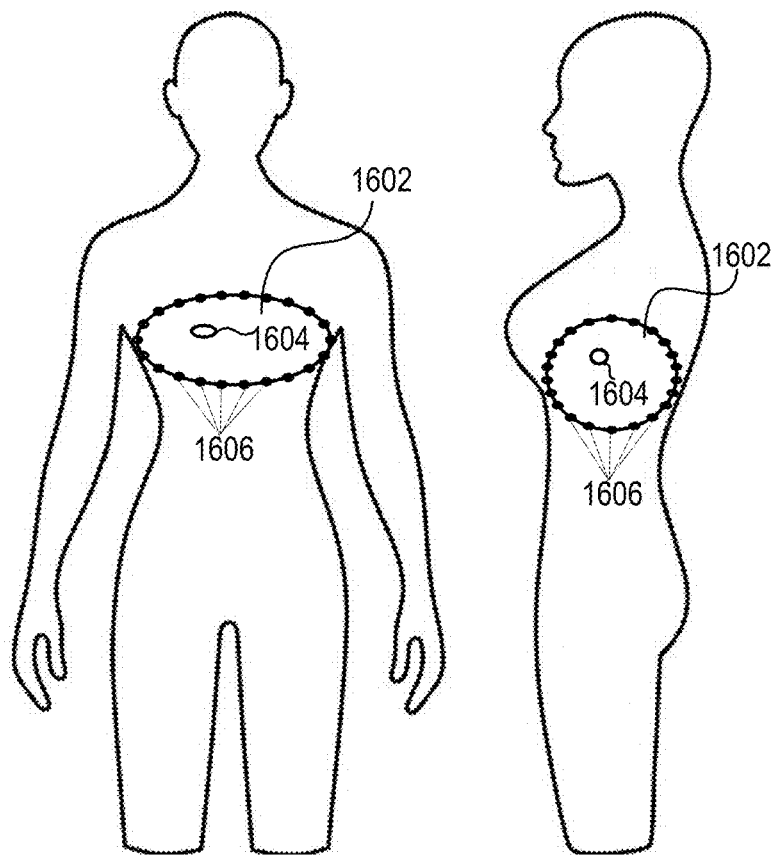
FIG. 16B shows an example transverse plan based on a center point of a tumor in a chest of a patient.

FIG. 16A shows a definition of the transverse plane 1602 in a head of a patient and FIG. 16B shows the transverse plane 1602 as defined in the chest of a patient. The transverse plane 1602 may be defined in any portion of the patient's body. The transverse plane 1602 may initially be defined by a center of the region of interest 1604 and an inclination angle. The inclination angle may be defined by skill in the art. By way of example, the inclination angle for the head may be 150-20 degrees off the axial plane (e.g., horizontal). The transverse plane 1602 may comprise a contour that is created by a boundary (e.g., outline) of the anatomical model (e.g., the head, the chest, the torso, the abdomen, the leg, the arm, and the like). For example, the contour may resemble an ellipse, a circle, an irregular shape, and the like. Determining the transverse plane 1602 may comprise determining a plurality of positions 1606 along the contour of the transverse plane 1602. The plurality of positions 1606 may represent one or more positions determined from fast approximations of electric field distributions (e.g., the output of the predictive engine at 1290, etc.) of potential transducer arrays placed according to the transverse plane 1602. Fast approximations may be used to determine that an electric field generated by a transducer array at each of the plurality of positions 1606 may be will pass through the ROI 1604. The plurality of positions 1606 may be determined based on fast approximations of electric field distributions (e.g., the output of the predictive engine at 1290, etc.). Any number of positions 1606 is contemplated. In some instances, the positions 1606 may be divided into pairs, such that an alternating electric field generated by a pair of transducer arrays (each transducer array located at one position of the pair of positions) will pass through the ROI 1604. The positions 1606 may be spaced apart, for example, by 15 degrees, corresponding to approximately 2 cm translations, giving a total of twelve different positions in the range of 180 degrees. Other spacings are contemplated.

The transverse plane may include the plurality of pairs of positions for the pair of transducer arrays along a contour of the plane. One or more positions of the plurality of pairs of positions may be adjusted based on the anatomical restriction to generate a modified plane. For each combination of a plurality of combinations of two pairs of transducer arrays, based on the electric field distribution map, a plurality of dose metrics in the ROI may be determined. The plurality of dose metrics may be based on a simulated electric field generated for each combination of the plurality of combinations of two pairs of transducer arrays.

In some instances, based on an angular restriction parameter and the plurality of dose metrics in the ROI, one or more candidate transducer array layout plans may be determined. In some instances, the angular restriction parameter may indicate an orthogonal angle between the plurality of pairs of transducer arrays. In some instances, the angular restriction parameter indicates a range of an angle between the plurality of pairs of transducer arrays. For optimization, the candidate transducer array layout plans may be compared to, associated with, and/or matched to the estimated one or more electric field distribution strength values for the pair of transducer arrays at each of a plurality of positions.

For each of the one or more candidate transducer array layout plans with close comparison to, are associated with, and/or matched to the estimated one or more electric field distribution strength values for the pair of transducer arrays at each of a plurality of positions, one or more adjusted candidate transducer array layout plans may be determined by adjusting a position or an orientation of one or more transducer arrays of the pair of transducer arrays. For each adjusted candidate transducer array layout plan, an adjusted dose metric in the ROI. Based on the adjusted dose metric in the ROI, a final transducer array layout plan may be determined from the adjusted candidate transducer array layout plans. In some instances, the accuracy of the predictive model may be readjusted (e.g., optimized, etc.) through further training if the final transducer array layout plan does not correlate to at least a portion of the one or more electric field distribution strength values for the pair of transducer arrays at each of a plurality of positions.

Once a three-dimensional array layout map (e.g., the final transducer array layout plan, etc.) has been determined for a patient, the delivery of TTFields may then be simulated by the patient modeling application 608 using the patient model. Simulated electric field distributions, dosimetry, and simulation-based analysis are described in U.S. Patent Publication No. 20190117956 A1 and Publication "Correlation of Tumor treating Fields Dosimetry to Survival Outcomes in Newly Diagnosed Glioblastoma: A Large-Scale Numerical Simulation-based Analysis of Data from the Phase 3 EF-14 randomized Trial" by Ballo, et al. (2019) which are incorporated herein by reference in their entirety.

To ensure systematic positioning of the transducer arrays relative to the tumor location, a reference coordinate system may be defined. For example, a transversal plane may initially be defined by conventional LR and AP positioning of the transducer arrays. The left-right direction may be defined as the x-axis, the AP direction may be defined as the y-axis, and the craniocaudal direction normal to the XY-plane may be defined as the z-axis.

After defining the coordinate system, transducer arrays may be virtually placed on the patient model with their centers and longitudinal axes in the XY-plane. A pair of transducer arrays may be systematically rotated around the z-axis of the head model, i.e. in the XY-plane, from 0 to 180 degrees, thereby covering the entire circumference of the head (by symmetry). The rotation interval may be, for example, 15 degrees, corresponding to approximately 2 cm translations, giving a total of twelve different positions in the range of 180 degrees. Other rotation intervals are contemplated. Electric field distribution calculations may be performed for each transducer array position relative to tumor coordinates.

Electric field distribution in the patient model may be determined by the patient modeling application 608 using a finite element (FE) approximation of electrical potential. In general, the quantities defining a time-varying electromagnetic field are given by the complex Maxwell equations. However, in biological tissues and at low to intermediate frequency of TTFields (f=200 kHz), the electromagnetic wavelength is much larger than the size of the head and the electric permittivity F is negligible compared to the real-valued electric conductivity σ, i.e., where ω=2πf is the angular frequency. This implies that the electromagnetic propagation effects and capacitive effects in the tissue are negligible, so the scalar electric potential may be well approximated by the static Laplace equation $\nabla \cdot (\sigma \nabla \phi) = 0$, with appropriate boundary conditions at the electrodes and skin. Thus, the complex impedance is treated as resistive (i.e. reactance is negligible) and currents flowing within the volume conductor are, therefore, mainly free (Ohmic) currents. The FE approximation of Laplace's equation was calculated using the SimNIBS software (simnibs.org). Computations were based on the Galerkin method and the residuals for the conjugate gradient solver were required to be <1E-9. Dirichlet boundary conditions were used with the electric potential was set to (arbitrarily chosen) fixed values at each set of electrode arrays. The electric (vector) field was calculated as the numerical gradient of the electric potential and the current density (vector field) was computed from the electric field using Ohm's law. The potential difference of the electric field values and the current densities were linearly rescaled to ensure a total peak-to-peak amplitude for each array pair of 1.8 A, calculated as the (numerical) surface integral of the normal current density components over all triangular surface elements on the active electrode discs. This corresponds to the current level used for clinical TTFields therapy by the Optune® device. The "dose" of TTFields was calculated as the intensity (L2 norm) of the field vectors. The modeled current is assumed to be provided by two separate and sequentially active sources each connected to a pair of 3×3 transducer arrays. The left and posterior arrays may be defined to be sources in the simulations, while the right and anterior arrays were the corresponding sinks, respectively. However, as TTFields employ alternating fields, this choice is arbitrary and does not influence the results.

An average electric field strength generated by transducer arrays placed at multiple locations on the patient may be determined by the patient modeling application 608 for one or more tissue types. In an aspect, the transducer array position that corresponds to the highest average electric field strength in the tumor tissue type(s) may be selected as a desired (e.g., optimal) transducer array position for the patient. In another aspect, one or more candidate positions for a transducer array(s) may be excluded as a result of a physical condition of the patient. For example, one or more candidate positions may be excluded based on areas of skin irritation, scars, surgical sites, discomfort, etc. Accordingly, the transducer array position that corresponds to the highest average electric field strength in the tumor tissue type(s), after excluding one or more candidate positions, may be selected as a desired (e.g., optimal) transducer array position for the patient. Thus, a transducer array position may be selected that results in less than the maximum possible average electric field strength.

The patient model may be modified to include an indication of the desired transducer array position. The resulting patient model, comprising the indication(s) of the desired transducer array position(s), may be referred to as the three-dimensional array layout map (e.g., three-dimensional array layout map 600). The three-dimensional array layout map may thus comprise a digital representation, in three-dimensional space, of the portion of the patient's body, an indication of tumor location, an indication of a position for placement of one or more transducer arrays, combinations thereof, and the like.

The three-dimensional array layout map may be provided to the patient in a digital form and/or a physical form. The patient, and/or a patient caregiver, may use the three-dimensional array layout map to affix one or more transducer arrays to an associated portion of the patient's body (e.g., head).

Figure 17:
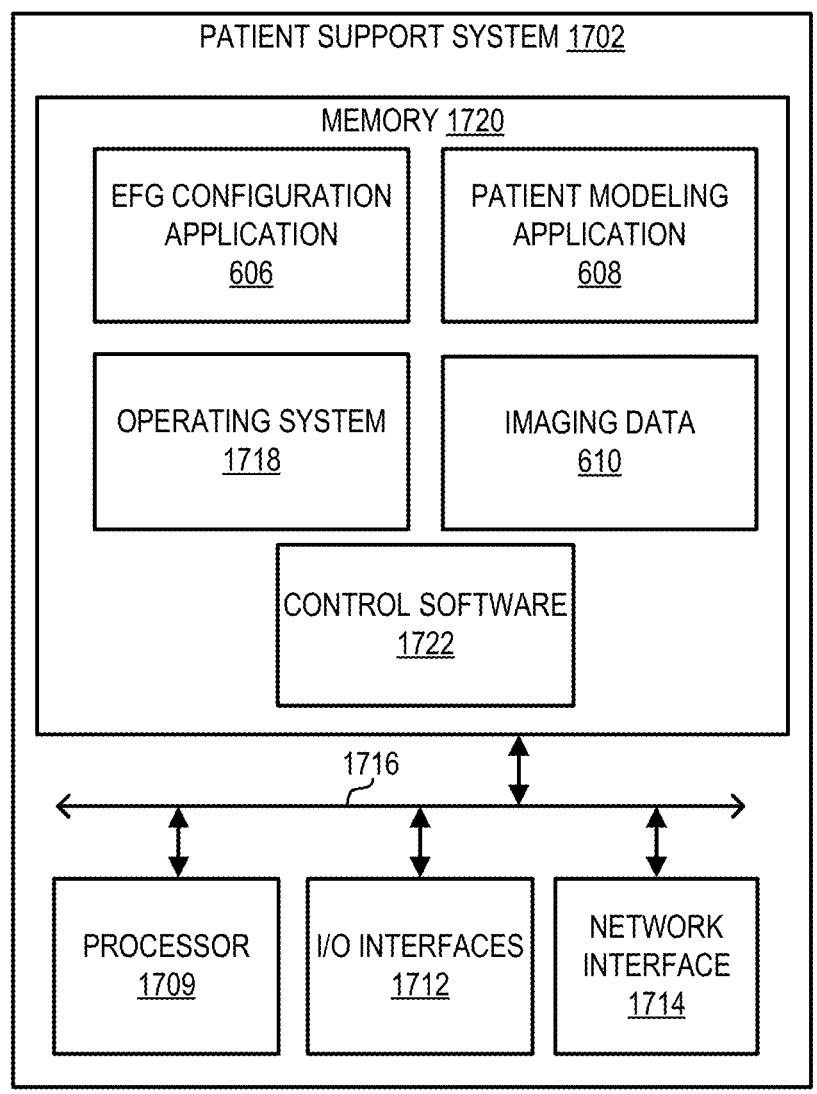
FIG. 17 is a block diagram depicting an example operating environment.

FIG. 17 is a block diagram depicting an environment 1700 comprising a non-limiting example of a patient support system 1702. In an aspect, some or all steps of any described method may be performed on a computing device as described herein. The patient support system 1702 can comprise one or multiple computers configured to store one or more of the EFG configuration application 606, the patient modeling application 608, the imaging data 610, and the like.

The patient support system 1702 can be a digital computer that, in terms of hardware architecture, generally includes a processor 1709, memory system 1720, input/output (I/O) interfaces 1712, and network interfaces 1714. These components (606, 608, 610, 1718, and 1722) are communicatively coupled via a local interface 1716. The local interface 1716 can be, for example, but not limited to, one or more buses or other wired or wireless connections, as is known in the art. The local interface 1716 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1709 can be a hardware device for executing software, particularly that stored in memory system 1720. The processor 1709 can be any custom made or commercially available processor, a central processing unit (CPU), an auxiliary processor among several processors associated with the patient support system 1702, a semiconductor-based microprocessor (in the form of a microchip or chipset), or generally any device for executing software instructions. When the patient support system 1702 is in operation, the processor 1709 can be configured to execute software stored within the memory system 1720, to communicate data to and from the memory system 1720, and to generally control operations of the patient support system 1702 pursuant to the software.

The I/O interfaces 1712 can be used to receive user input from and/or for providing system output to one or more devices or components. User input can be provided via, for example, a keyboard and/or a mouse. System output can be provided via a display device and a printer (not shown). I/O interfaces 1712 can include, for example, a serial port, a parallel port, a Small Computer System Interface (SCSI), an IR interface, an RF interface, and/or a universal serial bus (USB) interface.

The network interface 1714 can be used to transmit and receive from the patient support system 1702. The network interface 1714 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi), or any other suitable network interface device. The network interface 1714 may include address, control, and/or data connections to enable appropriate communications.

The memory system 1720 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 1720 may incorporate electronic, magnetic, optical, and/or other types of storage media. Note that the memory system 1720 can have a distributed architecture, where various components are situated remote from one another, but can be accessed by the processor 1709.

The software in memory system 1720 may include one or more software programs, each of which comprises an ordered listing of executable instructions for implementing logical functions. In the example of FIG. 17, the software in the memory system 1720 of the patient support system 1702 can comprise the EFG configuration application 606, the patient modeling application 608, the imaging data 610, and a suitable operating system (O/S) 1718. The operating system 1718 essentially controls the execution of other computer programs, and provides scheduling, input-output control, file and data management, memory management, and communication control and related services.

For purposes of illustration, application programs and other executable program components such as the operating system 1718 are illustrated herein as discrete blocks, although it is recognized that such programs and components can reside at various times in different storage components of the patient support system 1702. An implementation of the EFG configuration application 1706, the patient modeling application 608, the imaging data 610, and/or the control software 1720 can be stored on or transmitted across some form of computer-readable media. Any of the disclosed methods can be performed by computer readable instructions embodied on computer-readable media. Computer-readable media can be any available media that can be accessed by a computer. By way of example and not meant to be limiting, computer-readable media can comprise "computer storage media" and "communications media." "Computer storage media" can comprise volatile and non-volatile, removable and non-removable media implemented in any methods or technology for storage of information such as computer-readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

In an embodiment, illustrated in FIG. 18, one or more of the apparatus 100, the patient support system 602, the patient modeling application 608, the patient support system 1702, and/any other device/component described herein can be configured to perform a method 1800 comprising, at 1810, determining a plurality of sets of image data associated with a plurality of patients, wherein each patient is associated with a set of image data derived from imaging a portion of the patient, wherein each set of image data comprises a plurality of voxels, wherein each voxel of the plurality of voxels is labeled with a tissue type, and wherein each voxel of the plurality of voxels is labeled with an electric field strength distribution value (V cm-1) derived from a simulated application of an alternating electric field from of a pair of transducer arrays to the portion of the patient. For example, determining the plurality of sets of image data may comprise determining raw image data for each patient, wherein the raw image data comprises a plurality of voxels, assigning a tissue type to each voxel of the plurality of voxels, simulating, based on the tissue type of each voxel, application of an alternating electric field from a pair of transducer arrays at a plurality of positions within the raw image data, labeling each voxel of the plurality of voxels of the raw image data with the tissue type, the simulated electric fields, and the positions associated with the simulated electric fields; and generating, based on the labeled raw data, the plurality of sets of image data.

At 1820, determining, based on a first portion of the plurality of sets of image data, a plurality of features for a predictive model. For example, determining, based on the first portion of the plurality of sets of image data the plurality of features for the predictive model, may comprise a feature selection technique comprising one or more of a filter method, a wrapper method, or an embedded method. The plurality of features may comprise two or more of a conductivity value, a permittivity value, a distance to a closest transducer array, a distance to a closest conductive material, and/or the like.

At 1830, training, based on the plurality of features and the first portion of the plurality of sets of image data, the predictive model, wherein the predictive model is configured to estimate electric field strength distribution values. For example, training, based on the plurality of features and the first portion of the plurality of sets of image data, the predictive model may comprise a machine learning technique comprising one or more of discriminant analysis, a decision tree, a nearest neighbor (NN) algorithm (e.g., k-NN models, replicator NN models, etc.), a statistical algorithm (e.g., Bayesian networks, etc.), a clustering algorithm (e.g., k-means, mean-shift, etc.), neural networks (e.g., reservoir networks, artificial neural networks, etc.), support vector machines (SVMs), logistic regression algorithms, linear regression algorithms, Markov models or chains, principal component analysis (PCA) (e.g., for linear models), multilayer perceptron (MLP) ANNs (e.g., for non-linear models), replicating reservoir networks (e.g., for non-linear models, typically for time series), random forest classification, combinations thereof, and/or the like.

At 1840, testing, based on a second portion of the plurality of sets of image data, the predictive model.

At 1850, outputting, based on the testing, the predictive model. For example, the predictive model may be used for fast approximation of electric field distribution.

In some instances, the method 1800 may also comprise determining, for a new patient, a new set of image data, wherein the new set of image data comprises a plurality of voxels, presenting, to the predictive model, the new image data set, and estimating, by the predictive model, for each voxel of the plurality of voxels, one or more electric field distribution strength values for the pair of transducer arrays at each of a plurality of positions. In some instances, the method 1800 may also comprise selecting, based on the estimated one or more electric field distribution strength values, a position of the plurality of positions. In some instances, the method 1800 may also comprise determining, for each voxel of the plurality of voxels of the new image data set, a tissue type, and determining, for each voxel of the plurality of voxels of the new image data set, a conductivity value, a permittivity value, a distance to a closest transducer array, and a distance to a closest conductive material.

In an embodiment, illustrated in FIG. 19, one or more of the apparatus 100, the patient support system 602, the patient modeling application 608, the patient support system 1702, and/any other device/component described herein can be configured to perform a method 1900 comprising, at 1910, determining, for a patient, a set of image data, wherein the set of image data comprises a plurality of voxels.

At 1920, presenting, to a predictive model, the image data set, wherein the predictive model is configured to estimate electric field strength distribution values based on one or more simulated alternating electric fields from a pair of transducer arrays at a plurality of positions.

At 1930, estimating, by the predictive model, for each voxel of the plurality of voxels, one or more electric field distribution strength values for the pair of transducer arrays at each of a plurality of positions.

In some instances, the method 1900 may also comprise selecting, based on the estimated one or more electric field distribution strength values, a position of the plurality of positions. In some instances, the method 1900 may also comprise determining, for each voxel of the plurality of voxels of the image data set, a tissue type, and determining, for each voxel of the plurality of voxels of the image data set, a conductivity value, a permittivity value, a distance to a closest transducer array, and a distance to a closest conductive material.

At 1940, a transducer array map may be determined. For example, optimal locations for transducer arrays may be determined based on the set of image data, the estimated one or more electric field distribution strength values for the pair of transducer arrays at each of the plurality of positions, a region of interest (ROI) (e.g., tumor location, etc.) and anatomical parameters of the patient. The image data set may be used to determine a three-dimensional (3D) model of a portion of the patient's body. An electric field distribution map may be determined, based on the estimated one or more electric field distribution strength values for the pair of transducer arrays at each of a plurality of positions, for each of a plurality of positions for a pair of transducer arrays, based on the 3D model, the ROI, and an anatomical restriction associated with the patient.

The anatomical restriction may indicate one or more positions of a transverse plane of the ROI that should be excluded from use in determining the electric field distribution map. In some instances, the method may comprise determining, based on a center of the ROI, a plane that transverses the portion of the patient's body, wherein the plane comprises the plurality of pairs of positions for the pair of transducer arrays along a contour of the plane, and adjusting, based on the anatomical restriction parameter, one or more positions of the plurality of pairs of positions to generate a modified plane. For each combination of a plurality of combinations of two pairs of transducer arrays, based on the electric field distribution map, a plurality of dose metrics in the ROI may be determined. The plurality of dose metrics may be based on a simulated electric field generated for each combination of the plurality of combinations of two pairs of transducer arrays.

In some instances, the method may include determining, based on an angular restriction parameter and the plurality of dose metrics in the ROI, one or more candidate transducer array layout plans. In some instances, the angular restriction parameter may indicate an orthogonal angle between the plurality of pairs of transducer arrays. In some instances, the angular restriction parameter indicates a range of an angle between the plurality of pairs of transducer arrays. For optimization, the candidate transducer array layout plans may be compared to, associated with, and/or matched to the estimated one or more electric field distribution strength values for the pair of transducer arrays at each of a plurality of positions.

For each of the one or more candidate transducer array layout plans with close comparison to, are associated with, and/or matched to the estimated one or more electric field distribution strength values for the pair of transducer arrays at each of a plurality of positions, one or more adjusted candidate transducer array layout plans may be determined by adjusting a position or an orientation of one or more transducer arrays of the pair of transducer arrays. For each adjusted candidate transducer array layout plan, an adjusted dose metric in the ROI. Based on the adjusted dose metric in the ROI, a final transducer array layout plan may be determined from the adjusted candidate transducer array layout plans. In some instances, the accuracy of the predictive model may be readjusted (e.g., optimized, etc.) through further training if the final transducer array layout plan is does not correlate to at least a portion of the one or more electric field distribution strength values for the pair of transducer arrays at each of a plurality of positions.

In view of the described apparatuses, systems, and methods and variations thereof, herein below are described certain more particularly described embodiments of the invention. These particularly recited embodiments should not however be interpreted to have any limiting effect on any different claims containing different or more general teachings described herein, or that the "particular" embodiments are somehow limited in some way other than the inherent meanings of the language literally used therein.

Embodiment 1: A method comprising: determining a plurality of sets of image data associated with a plurality of patients, wherein each patient is associated with a set of image data derived from imaging a portion of the patient, wherein each set of image data comprises a plurality of voxels, wherein each voxel of the plurality of voxels is labeled with a tissue type, and wherein each voxel of the plurality of voxels is labeled with an electric field strength distribution value (V cm-1) derived from a simulated application of an alternating electric field from of a pair of transducer arrays to the portion of the patient, determining, based on a first portion of the plurality of sets of image data, a plurality of features for a predictive model, training, based on the plurality of features and the first portion of the plurality of sets of image data, the predictive model, wherein the predictive model is configured to estimate electric field strength distribution values, testing, based on a second portion of the plurality of sets of image data, the predictive model, and outputting, based on the testing, the predictive model.

Embodiment 2: The embodiment as in any one of the preceding embodiments wherein determining the plurality of sets of image data comprises: determining raw image data for each patient, wherein the raw image data comprises a plurality of voxels, assigning a tissue type to each voxel of the plurality of voxels, simulating, based on the tissue type of each voxel, application of an alternating electric field from a pair of transducer arrays at a plurality of positions within the raw image data, labeling each voxel of the plurality of voxels of the raw image data with the tissue type, the simulated electric fields, and the positions associated with the simulated electric fields, and generating, based on the labeled raw data, the plurality of sets of image data.

Embodiment 3: The embodiment as in any one of the preceding embodiments, wherein determining, based on the first portion of the plurality of sets of image data, the plurality of features for the predictive model comprises a feature selection technique comprising one or more of a filter method, a wrapper method, or an embedded method.

Embodiment 4: The embodiment as in any one of the preceding embodiments, wherein the plurality of features comprises two or more of a conductivity value, a permittivity value, a distance to a closest transducer array, or a distance to a closest conductive material.

Embodiment 5: The embodiment as in any one of the preceding embodiments, wherein training, based on the plurality of features and the first portion of the plurality of sets of image data, the predictive model comprises a machine learning technique comprising one or more of discriminant analysis, a decision tree, a nearest neighbor (NN) algorithm (e.g., k-NN models, replicator NN models, etc.), a statistical algorithm (e.g., Bayesian networks, etc.), a clustering algorithm (e.g., k-means, mean-shift, etc.), neural networks (e.g., reservoir networks, artificial neural networks, etc.), support vector machines (SVMs), logistic regression algorithms, linear regression algorithms, Markov models or chains, principal component analysis (PCA) (e.g., for linear models), multi-layer perceptron (MLP) ANNs (e.g., for non-linear models), replicating reservoir networks (e.g., for non-linear models, typically for time series), or random forest classification.

Embodiment 6: The embodiment as in any one of the preceding embodiments, further comprising determining, for a new patient, a new set of image data, wherein the new set of image data comprises a plurality of voxels, presenting, to the predictive model, the new image data set, and estimating, by the predictive model, for each voxel of the plurality of voxels, one or more electric field distribution strength values for the pair of transducer arrays at each of a plurality of positions.

Embodiment 7: The embodiment as in any one of the preceding embodiments further comprising selecting, based on the estimated one or more electric field distribution strength values, a position of the plurality of positions.

Embodiment 8: The embodiment as in any one of the preceding embodiments further comprising determining, for each voxel of the plurality of voxels of the new image data set, a tissue type, and determining, for each voxel of the plurality of voxels of the new image data set, a conductivity value, a permittivity value, a distance to a closest transducer array, and a distance to a closest conductive material.

Embodiment 9: The embodiment as in any one of the preceding embodiments further comprising using the predictive model.

Embodiment 10: A method comprising: determining, for a patient, a set of image data, wherein the set of image data comprises a plurality of voxels, presenting, to a predictive model, the image data set, wherein the predictive model is configured to estimate electric field strength distribution values based on one or more simulated alternating electric fields from a pair of transducer arrays at a plurality of positions, estimating, by the predictive model, for each voxel of the plurality of voxels, one or more electric field distribution strength values for the pair of transducer arrays at each of a plurality of positions, and determining, based on the estimated one or more electric field distribution strength values for the pair of transducer arrays at each of the plurality of positions, a region of interest, and an anatomical restriction associated with the patient, a transducer array map comprising one or more positions of the plurality of positions.

Embodiment 11: The embodiment as in embodiment 10 further comprising selecting, based on the estimated one or more electric field distribution strength values, a position of the plurality of positions.

Embodiment 12: The embodiments as in embodiments 10-11, further comprising determining, for each voxel of the plurality of voxels of the image data set, a tissue type, and determining, for each voxel of the plurality of voxels of the image data set, a conductivity value, a permittivity value, a distance to a closest transducer array, and a distance to a closest conductive material.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification While the methods and systems have been described in connection with preferred embodiments and specific examples, it is not intended that the scope be limited to the particular embodiments set forth, as the embodiments herein are intended in all respects to be illustrative rather than restrictive.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
   determining a plurality of sets of image data associated with a plurality of patients, wherein each patient is associated with a set of image data derived from imaging a portion of the patient, wherein each set of image data comprises a plurality of voxels, wherein each voxel of the plurality of voxels is labeled with a tissue type, and wherein each voxel of the plurality of voxels is labeled with an electrical field strength distribution value derived from a simulated application of an alternating electrical field from a pair of transducer arrays to the portion of the patient;
   determining, based on a first portion of the plurality of sets of image data, a plurality of features for a predictive model;
   training, based on the plurality of features and the first portion of the plurality of sets of image data, the predictive model, wherein the predictive model is trained to estimate electric field strength distribution values;
   testing, based on a second portion of the plurality of sets of image data, the predictive model; and
   outputting, based on the testing, the predictive model.

2. The method of claim 1, wherein determining the plurality of sets of image data comprises:
   determining raw image data for each patient, wherein the raw image data comprises a plurality of voxels;
   assigning a tissue type to each voxel of the plurality of voxels;
   simulating, based on the tissue type of each voxel, application of an alternating electric field from a pair of transducer arrays at a plurality of positions within the raw image data;
   labeling each voxel of the plurality of voxels of the raw image data with the tissue type, the simulated electric fields, and the positions associated with the simulated electric fields; and
   generating, based on the labeled raw data, the plurality of sets of image data.

3. The method of claim 1, wherein determining, based on the first portion of the plurality of sets of image data, the plurality of features for the predictive model comprises the feature selection technique comprising one or more of a filter method, a wrapper method, or an embedded method.

4. The method of claim 1, wherein the plurality of features comprises two or more of a conductivity value, a permittivity value, a distance to a closest transducer array, or a distance to a closest conductive material.

5. The method of claim 1, wherein training, based on the plurality of features and the first portion of the plurality of sets of image data, the predictive model comprises a machine learning technique comprising one or more of discriminant analysis, a decision tree, a statistical algorithm, or a neural network.

6. The method of claim 1, further comprising:
   determining, for a new patient, a new set of image data, wherein the new set of image data comprises a plurality of voxels;
   presenting, to the predictive model, the new image data set; and
   estimating, by the predictive model, for each voxel of the plurality of voxels, one or more electric field distribution strength values for the pair of transducer arrays at each of a plurality of positions.

7. The method of claim 6, further comprising selecting, based on the estimated one or more electric field distribution strength values, a position of the plurality of positions.

8. The method of claim 6, further comprising:
   determining, for each voxel of the plurality of voxels of the new image data set, a tissue type; and
   determining, for each voxel of the plurality of voxels of the new image data set, a conductivity value, a permittivity value, a distance to a closest transducer array, and a distance to a closest conductive material.

9. The method of claim 6, wherein the plurality of features comprise a feature selection technique comprising an electric field distribution rule.

10. The method of claim 1, wherein determining the plurality of features for the predictive model comprises extracting the plurality of features from the first portion of the plurality of sets of image data.

11. The method of claim 10, wherein the plurality of features for the predictive model extracted from the first portion of the plurality of sets of image data comprise tissue types of the first portion of the plurality of sets of image data.

12. An apparatus comprising:
   one or more processors; and
   memory storing processor-executable instructions that, when executed by the one or more processors, cause the apparatus to:
   determine a plurality of sets of image data associated with a plurality of patients, wherein each patient is associated with a set of image data derived from imaging a portion of the patient, wherein each set of image data comprises a plurality of voxels, wherein each voxel of the plurality of voxels is labeled with a tissue type, and wherein each voxel of the plurality of voxels is labeled with an electrical field strength distribution value derived from a simulated application of an alternating electrical field from a pair of transducer arrays to the portion of the patient;
   determine, based on a first portion of the plurality of sets of image data, a plurality of features for a predictive model;
   train, based on the plurality of features and the first portion of the plurality of sets of image data, the predictive model, wherein the predictive model is trained to estimate electrical field strength distribution values;
   test, based on a second portion of the plurality of sets of image data, the predictive model; and
   output, based on the testing, the predictive model.

13. The apparatus of claim 12, wherein the processor-executable instructions that, when executed by the one or more processors, cause the apparatus to determine the plurality of sets of image data further cause the apparatus to:
   determine raw image data for each patient, wherein the raw image data comprises a plurality of voxels;

assign a tissue type to each voxel of the plurality of voxels;

simulate, based on the tissue type of each voxel, application of an alternating electrical field from a pair of transducer arrays at a plurality of positions within the raw image data;

label each voxel of the plurality of voxels of the raw image data with the tissue type, the simulated electrical fields, and the positions associated with the simulated electrical fields; and generate, based on the labeled raw data, the plurality of sets of image data.

14. The apparatus of claim 12, wherein the processor-executable instructions that, when executed by the one or more processors, cause the apparatus to determine, based on the first portion of the plurality of sets of image data, the plurality of features for the predictive model further cause the apparatus to determine the plurality of features for the predictive model based on the feature selection technique comprising one or more of a filter method, a wrapper method, or an embedded method.

15. The apparatus of claim 12, wherein the plurality of features comprises two or more of a conductivity value, a permittivity value, a distance to a closest transducer array, or a distance to a closest conductive material.

16. The apparatus of claim 12, wherein the processor-executable instructions that, when executed by the one or more processors, cause the apparatus to train, based on the plurality of features and the first portion of the plurality of sets of image data, the predictive model further cause the apparatus to train the predictive model based on a machine learning technique comprising one or more of discriminant analysis, a decision tree, a statistical algorithm, or a neural network.

17. The apparatus of claim 12, wherein the processor-executable instructions, when executed by the one or more processors, further cause the apparatus to:

determine, for a new patient, a new set of image data, wherein the new set of image data comprises a plurality of voxels;

present, to the predictive model, the new image data set; and estimate, by the predictive model, for each voxel of the plurality of voxels, one or more electrical field distribution strength values for the pair of transducer arrays at each of a plurality of positions.

18. The apparatus of claim 17, wherein the processor-executable instructions, when executed by the one or more processors, further cause the apparatus to select, based on the estimated one or more electrical field distribution strength values, a position of the plurality of positions.

19. The apparatus of claim 17, wherein the processor-executable instructions, when executed by the one or more processors, further cause the apparatus to:

determine, for each voxel of the plurality of voxels of the new image data set, a tissue type; and determine, for each voxel of the plurality of voxels of the new image data set, a conductivity value, a permittivity value, a distance to a closest transducer array, and a distance to a closest conductive material.

20. The apparatus of claim 17, wherein the plurality of features comprise a feature selection technique comprising an electric field distribution rule.

* * * * *